US012064270B2

(12) United States Patent
Kang et al.

(10) Patent No.: US 12,064,270 B2
(45) Date of Patent: Aug. 20, 2024

(54) APPARATUS FOR BLOOD PRESSURE ESTIMATION USING PHOTOPLETHYSMOGRAPHY AND CONTACT PRESSURE

(71) Applicant: SAMSUNG ELECTRONICS CO., LTD., Suwon-si (KR)

(72) Inventors: Jae Min Kang, Seoul (KR); Yong Joo Kwon, Yongin-si (KR); Seung Woo Noh, Seongnam-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/559,721

(22) Filed: Dec. 22, 2021

(65) Prior Publication Data

US 2022/0110535 A1    Apr. 14, 2022

Related U.S. Application Data

(62) Division of application No. 16/164,076, filed on Oct. 18, 2018, now Pat. No. 11,241,197.

(30) Foreign Application Priority Data

Oct. 18, 2017 (KR) .................. 10-2017-0135384
Sep. 18, 2018 (KR) .................. 10-2018-0111192

(51) Int. Cl.
*A61B 5/00*    (2006.01)
*A61B 5/02*    (2006.01)
(Continued)

(52) U.S. Cl.
CPC ........ *A61B 5/7278* (2013.01); *A61B 5/02007* (2013.01); *A61B 5/02108* (2013.01);
(Continued)

(58) Field of Classification Search
CPC .............. A61B 5/7278; A61B 5/02007; A61B 5/02108; A61B 5/02116; A61B 5/02125;
(Continued)

(56) References Cited

U.S. PATENT DOCUMENTS

| 4,926,873 A | 5/1990 | Frankenreiter |
| 6,394,959 B1 | 5/2002 | Takaya |

(Continued)

FOREIGN PATENT DOCUMENTS

| CN | 107072562 A | 8/2017 |
| EP | 3 213 678 A1 | 9/2017 |

(Continued)

OTHER PUBLICATIONS

Communication dated Aug. 19, 2022, issued by the China National Intellectual Property Administration in Chinese Application No. 201811208893.3.

(Continued)

*Primary Examiner* — Patrick Fernandes
*Assistant Examiner* — Marjan Saboktakin
(74) *Attorney, Agent, or Firm* — Sughrue Mion, PLLC

(57) ABSTRACT

An apparatus for estimating cardiovascular information includes: a main body; and a strap connected to the main body and formed to be flexible to be wrapped around an object, wherein the main body may include: a pulse wave measurer configured to measure, from the subject, a first pulse wave signal by using a first light of a first wavelength, and a second pulse wave signal by using a second light of a second wavelength, the first wavelength being different from the second wavelength; a contact pressure measurer configured to measure a contact pressure between the object and the pulse wave measurer; and a processor configured to extract a cardiovascular characteristic value based on the first pulse wave signal, the second pulse wave signal, and (Continued)

change in the contact pressure, and estimate cardiovascular information based on the extracted cardiovascular characteristic value.

8 Claims, 18 Drawing Sheets

(51) Int. Cl.
*A61B 5/021* (2006.01)
*A61B 5/022* (2006.01)
*A61B 5/024* (2006.01)
*A61B 5/026* (2006.01)
*A61B 5/029* (2006.01)
*A61B 5/145* (2006.01)
*G16H 10/00* (2018.01)
*G16H 40/63* (2018.01)
*G16H 50/20* (2018.01)
*G16H 50/50* (2018.01)

(52) U.S. Cl.
CPC ...... *A61B 5/02116* (2013.01); *A61B 5/02125* (2013.01); *A61B 5/022* (2013.01); *A61B 5/0261* (2013.01); *A61B 5/029* (2013.01); *A61B 5/14532* (2013.01); *A61B 5/681* (2013.01); *A61B 5/6831* (2013.01); *A61B 5/6843* (2013.01); *G16H 10/00* (2018.01); *G16H 40/63* (2018.01); *G16H 50/20* (2018.01); *G16H 50/50* (2018.01); *A61B 5/02416* (2013.01); *A61B 2562/0219* (2013.01); *A61B 2562/0247* (2013.01); *A61B 2562/0252* (2013.01)

(58) Field of Classification Search
CPC ....... A61B 5/022; A61B 5/0261; A61B 5/029; A61B 5/14532; A61B 5/681; A61B 5/6831; A61B 5/6843
See application file for complete search history.

(56) References Cited

U.S. PATENT DOCUMENTS

| 10,582,861 | B2 | 3/2020 | Kitagawa et al. | |
|---|---|---|---|---|
| 2004/0059236 | A1 | 3/2004 | Margulies et al. | |
| 2010/0210956 | A1 | 8/2010 | Im | |
| 2013/0296714 | A1* | 11/2013 | Kassim | G01N 21/3151 |
| | | | | 600/479 |
| 2015/0018637 | A1* | 1/2015 | Chen | A61B 5/0295 |
| | | | | 600/301 |
| 2016/0000339 | A1 | 1/2016 | Kang et al. | |
| 2017/0119262 | A1 | 5/2017 | Shim et al. | |
| 2017/0119293 | A1 | 5/2017 | Matsui | |
| 2017/0224226 | A1 | 8/2017 | Kitagawa et al. | |
| 2018/0338721 | A1* | 11/2018 | Wang | A61B 5/0205 |
| 2019/0059752 | A1* | 2/2019 | Botsva | A61B 5/332 |
| 2019/0104997 | A1 | 4/2019 | Kang et al. | |
| 2019/0336016 | A1* | 11/2019 | Zhao | A61B 5/7203 |

FOREIGN PATENT DOCUMENTS

| EP | 3469984 | A1 | 4/2019 | |
|---|---|---|---|---|
| JP | 2005342163 | A | 12/2005 | |
| JP | 2006239114 | A | 9/2006 | |
| JP | 2011200610 | A | 10/2011 | |
| JP | 2016220886 | A | 12/2016 | |
| KR | 1020060081187 | A | 7/2006 | |
| KR | 1020060116635 | A | 11/2006 | |
| KR | 1020080098989 | A | 11/2008 | |
| KR | 100877207 | B1 | 1/2009 | |
| KR | 101039473 | B1 | 6/2011 | |
| KR | 10-2016-0126232 | A | 11/2016 | |
| KR | 1020170009658 | A | 1/2017 | |
| KR | 10-2017-0049279 | A | 5/2017 | |
| KR | 10-2019-0040527 | A | 4/2019 | |
| WO | 2017/152098 | A1 | 9/2017 | |
| WO | WO-2019053276 | A1 * | 3/2019 | ........... A61B 5/0053 |

OTHER PUBLICATIONS

Communication dated Feb. 10, 2021, from the European Patent Office in European Application No. 18200945.6.
Communication issued Dec. 13, 2021 by the Korean Intellectual Property Office in Korean Patent Application No. 10-2016-0126232.
Jeong, Incheol, "Optical Non-invasive Blood Pressure: PPG Waveform-based Estimation and Verification", The Graduate School, Yonsei University, Department of Biomedical Engineering, Dec. 1, 2010, pp. 1-126, XP055558061. (141 pages total).
Santos, Pedro et al., "Photoplethysmographic Logger with Contact Force and Hydrostatic Pressure Monitoring", Bioengineering (Enbeng), 2013 IEEE 3rd Portuguese Meeting in, IEEE, Feb. 20, 2013, pp. 1-6, XP032410163. (6 pages total).
Search Report issued Feb. 26, 2019 by the European Patent Office in counterpart European Patent Application No. 18200945.6.
Fallow BA, Tarumi T, Tanaka H., Influence of skin type and wavelength on light wave reflective. J Clin Minit Comput. Jun. 2013; 27(3):313-7. doi: 10.107/s10877-013-9436-7. Epub Feb. 9, 2013. PMID:23397431. (Year:2013).

* cited by examiner

APPARATUS FOR BLOOD PRESSURE ESTIMATION USING PHOTOPLETHYSMOGRAPHY AND CONTACT PRESSURE

CROSS-REFERENCE TO RELATED APPLICATION(S)

This application is a divisional application of U.S. application Ser. No. 16/164,076 filed Oct. 18, 20018, which claims priority from Korean Patent Application No. 10-2017-0135384, filed on Oct. 18, 2017, and Korean Patent Application No. 10-2018-0111192, filed on Sep. 18, 2018, in the Korean Intellectual Property Office, the disclosures of which are incorporated herein by reference in their entireties.

BACKGROUND

1. Field

Apparatuses and methods consistent with exemplary embodiments relate to estimating cardiovascular information.

2. Description of the Related Art

Generally, a cuff-based measurement method and a cuffless measurement method are used as a non-invasive method of estimating cardiovascular information such as blood pressure and the like. The cuff-based measurement method includes: a method of measuring blood pressure by winding a cuff around an upper arm and hearing the sound of blood vessels through a stethoscope during inflation and deflation of the cuff, and an Oscillometric method which includes measuring pressure signals during inflation/deflation of the cuff using an automated device and measuring blood pressure based on a point of maximum pressure signal change. As the cuffless measurement method, there is a Pulse Transit Time (PTT) method of estimating blood pressure by using pulse wave velocity, and a Pulse Wave Analysis (PWA) method of estimating blood pressure by pulse wave form analysis.

According to the cuff-based measurement method, cuff pressure may cause pain to a subject. In the cuffless measurement method, including PTT method and the PWA method, blood pressure is estimated based on pulse waves, such that accuracy of measurement cannot be guaranteed.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments provide an apparatus and method for estimating cardiovascular information.

According to an aspect of an exemplary embodiment, there is provided an apparatus for estimating cardiovascular information including: a pulse wave measurer configured to measure, from an object, a first pulse wave signal by using a first light of a first wavelength and a second pulse wave signal by using a second light of a second wavelength, the first wavelength being different from the second wavelength; a contact pressure measurer configured to measure a contact pressure between the object and the pulse wave measurer; and a processor configured to extract a cardiovascular characteristic value based on the first pulse wave signal, the second pulse wave signal, and a change in the contact pressure, and estimate cardiovascular information based on the extracted cardiovascular characteristic value.

The pulse wave measurer may include: a light source configured to emit the first light and the second light onto the object; and a photodetector configured to measure the first pulse wave signal and the second pulse wave signal by receiving the first light and the second light which are reflected or scattered from the object, respectively.

The contact pressure measurer may measure the contact pressure by using at least one of a force sensor, a pressure sensor, an acceleration sensor, a piezoelectric film, a load cell, radar, and a photoplethysmography (PPG) sensor.

The processor may detect a contact pressure transition period based on the contact pressure, may extract at least one pulse wave feature point based on the first pulse wave signal and the second pulse wave signal in the contact pressure transition period, and may extract the cardiovascular characteristic value by using at least one of a pulse wave characteristic value and a contact pressure value which correspond to the at least one pulse wave feature point.

The contact pressure transition period may include a contact pressure increasing period and a contact pressure decreasing period.

The processor may extract, as the at least one pulse wave feature point, at least one of a valley point and a peak point of a first pulse wave direct current (DC) component signal in the contact pressure transition period, a valley point and a peak point of a second pulse wave DC component signal in the contact pressure transition period, a valley point and a peak point of a differentiated first pulse wave DC component signal in the contact pressure transition period, a valley point and a peak point of a differentiated second pulse wave DC component signal in the contact pressure transition period, a valley point and a peak point of a first pulse wave alternating current (AC) component signal in the contact pressure transition period, a valley point and a peak point of a second pulse wave AC component signal in the contact pressure transition period, a valley point and a peak point of a DC component differential signal in the contact pressure transition period, and a valley point and a peak point of a differentiated DC component differential signal in the contact pressure transition period.

The processor may extract the cardiovascular characteristic value based on at least one of T1, T2, T3, T4, T5, T6, T7, T8, T9, T10, T11, T12, T13, T14, T15, T16, T17, T18, T19, T20, T21, T22, T23, T24, A1, A2, A3, A4, A5, A6, A7, A8, A9, A10, A11, A12, A13, A14, A15, A16, A17, A18, A19, A20, A21, A22, P1, P2, P3, P4, P5, P6, P7, P8, P9, P10, P11, P12, P13, P14, P15, P16, P17, P18, P19, P20, P21, P22, P23, P24, Pgmax, and Pgmin of the first pulse wave signal and the second pulse wave signal.

T1 may denote time of a valley point of a first pulse wave DC component signal in a contact pressure increasing period; T2 may denote time of a peak point of a first pulse wave DC component signal in the contact pressure increasing period; T3 may denote time of a valley point of a second pulse wave DC component signal in the contact pressure increasing period; T4 may denote time of a peak point of the second pulse wave DC component signal in the contact pressure increasing period; T5 may denote time of a valley point of the first pulse wave DC component signal in a contact pressure decreasing period; T6 may denote time of a peak point of the first pulse wave DC component signal in the contact pressure decreasing period; T7 may denote time of a valley point of the second pulse wave DC component signal in the contact pressure decreasing period; T8 may denote time of a peak point of the second pulse wave DC component signal in the contact pressure decreasing period; T9 may denote time of a valley point of a differentiated first pulse wave DC component signal in the contact pressure increasing period; T10 may denote time of a valley point of the differentiated second pulse wave DC component signal in the contact pressure increasing period; T11 may denote time of a peak point of the differentiated first pulse wave DC component signal in the contact pressure decreasing period; T12 may denote time of a peak point of the differentiated second pulse wave DC component signal in the contact pressure decreasing period; T13 may denote time of a peak point of a first pulse wave AC component signal in a contact pressure increasing period; T14 may denote time of a peak point of the second pulse wave AC component signal in the contact pressure increasing period; T15 may denote time of a valley point of a first pulse wave AC component signal in a contact pressure decreasing period; T16 may denote time of a valley point of the second pulse wave AC component signal in a contact pressure decreasing period; T17 may denote time of a peak point of a DC component differential signal in the contact pressure increasing period; T18 may denote time of a valley point of the DC component differential signal in the contact pressure increasing period; T19 may denote time of a peak point of a differentiated DC component differential signal in the contact pressure increasing period; T20 may denote time of a valley point of the DC component differential signal in the contact pressure decreasing period; T21 may denote time of a peak point of a DC component differential signal in the contact pressure decreasing period; T22 may denote time of a valley point of the differentiated DC component differential signal in the contact pressure decreasing period; T23 may denote time when the contract pressure starts to increase; T24 may denote time when the contract pressure starts to decrease; A1 may denote an amplitude of the first pulse wave DC component signal at T1; A2 may denote an amplitude of the first pulse wave DC component signal at T2; A3 may denote an amplitude of the second pulse wave DC component signal at T3; A4 may denote an amplitude of the second pulse wave DC component signal at T4; A5 may denote an amplitude of the first pulse wave DC component signal at T5; A6 may denote an amplitude of the first pulse wave DC component signal at T6; A7 may denote an amplitude of the second pulse wave DC component signal at T7; A8 may denote an amplitude of the second pulse wave DC component signal at T8; A9 may denote an amplitude of the differentiated first pulse wave DC component signal at T9; A10 may denote an amplitude of the differentiated second pulse wave DC component signal T10; A11 may denote an amplitude of the differentiated first pulse wave DC component signal T11; A12 may denote an amplitude of the differentiated second pulse wave DC component signal T12; A13 may denote an amplitude of the first pulse wave AC component signal T13; A14 may denote an amplitude of the second pulse wave AC component signal at T14; A15 may denote an amplitude of the first pulse wave AC component signal at T15; A16 may denote an amplitude of the second pulse wave AC component signal at T16; A17 may denote an amplitude of the DC component differential signal at T17; A18 may denote an amplitude of the DC component differential signal at T18; A19 may denote an amplitude of the differentiated DC component differential signal at T19; A20 may denote an amplitude of the DC component differential signal at T20; A21 may denote an amplitude of the DC component differential signal at T21; A22 may denote an amplitude of the differentiated DC component differential signal at T22; P1 may denote a contact pressure magnitude at T1; P2 may denote a contact pressure magnitude at T2; P3 may denote a contact pressure magnitude at T3; P4 may denote a contact pressure magnitude at T4; P5 may denote a contact pressure magnitude at T5; P6 may denote a contact pressure magnitude at T6; P7 may denote a contact pressure magnitude at T7; P8 may denote a contact pressure magnitude at T8; P9 may denote a contact pressure magnitude at T9; P10 may denote a contact pressure magnitude at T10; P11 may denote a contact pressure magnitude at T11; P12 may denote a contact pressure magnitude at T12; P13 may denote a contact pressure magnitude at T13; P14 may denote a contact pressure magnitude at T14; P15 may denote a contact pressure magnitude at T15; P16 may denote a contact pressure magnitude at T16; P17 may denote a contact pressure magnitude at T17; P18 may denote a contact pressure magnitude at T18; P19 may denote a contact pressure magnitude at T19; P20 may denote a contact pressure magnitude at T20; P21 may denote a contact pressure magnitude at T21; P22 may denote a contact pressure magnitude at T22; P23 may denote a contact pressure magnitude at T23; P24 may denote a contact pressure magnitude at T24; Pgmax may denote a maximum value of a contact pressure gradient in the contact pressure increasing period; and Pgmin may denote a minimum value of a contact pressure gradient in the contact pressure decreasing period.

The cardiovascular information may include at least one of blood pressure, vascular age, arterial stiffness, cardiac output, vascular compliance, blood glucose, blood triglycerides, and peripheral vascular resistance.

The object may be a user of the apparatus, and the processor may generate guide information for guiding the user to increase or decrease the contact pressure.

The apparatus for estimating cardiovascular information may further include an actuator configured to control the contact pressure between the object and the pulse wave measurer.

The apparatus for estimating cardiovascular information may further include a communication interface configured to transmit, to an external device, at least one of the first pulse wave signal, the second pulse wave signal, the contact pressure, the pulse wave feature point, the cardiovascular characteristic value, and the cardiovascular information.

The apparatus for estimating cardiovascular information may further include an output interface configured to output the cardiovascular information to an external device.

The apparatus for estimating cardiovascular information may be implemented in one of a cellular phone, a smartphone, a tablet personal computer (PC), a laptop computer, a personal digital assistant (PDA), a portable multimedia player (PMP), a navigation, an MP3 player, a digital camera, and a wearable device.

According to an aspect of another exemplary embodiment, there is provided a wearable device including: a main body; and a strap connected to the main body and formed to be flexible to be wrapped around an object, wherein the main body may include: a pulse wave measurer configured to measure, from the subject, a first pulse wave signal by using a first light of a first wavelength, and a second pulse wave signal by using a second light of a second wavelength, the first wavelength being different from the second wavelength; a contact pressure measurer configured to measure a contact pressure between the object and the pulse wave measurer; and a processor configured to extract a cardiovascular characteristic value based on the first pulse wave signal, the second pulse wave signal, and a change in the contact pressure, and estimate cardiovascular information based on the extracted cardiovascular characteristic value.

The processor may detect a contact pressure transition period based on the contact pressure, may extract at least one pulse wave feature point based on the first pulse wave signal and the second pulse wave signal in the contact pressure transition period, and may extract the cardiovascular characteristic value by using at least one of a pulse wave characteristic value and a contact pressure value which correspond to the at least one pulse wave feature point.

The main body may further include an actuator configured to control the contact pressure between the object and the pulse wave measurer by adjusting a length of the strap.

According to an aspect of another exemplary embodiment, there is provided a method of estimating cardiovascular information by using a pulse wave measurer. The method may include: measuring a first pulse wave signal from an object by using a first light of a first wavelength; measuring a second pulse wave signal from the object by using a second light of a second wavelength; measuring a contact pressure between the object and the pulse wave measurer; extracting a cardiovascular characteristic value based on the first pulse wave signal, the second pulse wave signal, and a change in the contact pressure; and estimating cardiovascular information based on the extracted cardiovascular characteristic value.

The measuring the first pulse wave signal and the measuring the second pulse wave signal may include: emitting the first light and the second light onto the object; and measuring the first pulse wave signal and the second pulse wave signals by receiving the first light and the second light which are reflected or scattered from the object, respectively.

The measuring the first pulse wave signal and the second pulse wave signal may include: emitting, light of different wavelengths onto the object; and measuring the pulse wave signals by receiving light reflected or scattered from the object.

The measuring the contact pressure may include measuring the contact pressure by using at least one of a force sensor, a pressure sensor, an acceleration sensor, a piezoelectric film, a load cell, radar, and a photoplethysmography (PPG) sensor.

The extracting the cardiovascular characteristic value may include: detecting a contact pressure transition period based on the contact pressure; extracting at least one pulse wave feature point based on the first pulse wave signal and the second pulse wave signal in the contact pressure transition period; and extracting the cardiovascular characteristic value by using at least one of a pulse wave characteristic value and a contact pressure value which correspond to the at least one pulse wave feature point.

The contact pressure transition period may include a contact pressure increasing period and a contact pressure decreasing period.

The extracting the at least one pulse wave feature point may include extracting, as the at least one pulse wave feature point, at least one of a valley point and a peak point of a first pulse wave DC component signal in the contact pressure transition period, a valley point and a peak point of a second pulse wave DC component signal in the contact pressure transition period, a valley point and a peak point of a differentiated first pulse wave DC component signal in the contact pressure transition period, a valley point and a peak point of a differentiated second pulse wave DC component signal in the contact pressure transition period, a valley point and a peak point of a first pulse wave AC component signal in the contact pressure transition period, a valley point and a peak point of a second pulse wave AC component signal in the contact pressure transition period, a valley point and a peak point of a DC component differential signal in the contact pressure transition period, and a valley point and a peak point of a differentiated DC component differential signal in the contact pressure transition period.

The extracting of the cardiovascular characteristic value may include extracting the cardiovascular characteristic value by combining at least one or two or more of T1, T2, T3, T4, T5, T6, T7, T8, T9, T10, T11, T12, T13, T14, T15, T16, T17, T18, T19, T20, T21, T22, T23, T24, A1, A2, A3, A4, A5, A6, A7, A8, A9, A10, A11, A12, A13, A14, A15, A16, A17, A18, A19, A20, A21, A22, P1, P2, P3, P4, P5, P6, P7, P8, P9, P10, P11, P12, P13, P14, P15, P16, P17, P18, P19, P20, P21, P22, P23, P24, Pgmax, and Pgmin of the first pulse wave signal and the second pulse wave signal.

T1 may denote time of a valley point of a first pulse wave DC component signal in a contact pressure increasing period; T2 may denote time of a peak point of a first pulse wave DC component signal in the contact pressure increasing period; T3 may denote time of a valley point of a second pulse wave DC component signal in the contact pressure increasing period; T4 may denote time of a peak point of the second pulse wave DC component signal in the contact pressure increasing period; T5 may denote time of a valley point of the first pulse wave DC component signal in a contact pressure decreasing period; T6 may denote time of a peak point of the first pulse wave DC component signal in the contact pressure decreasing period; T7 may denote time of a valley point of the second pulse wave DC component signal in the contact pressure decreasing period; T8 may denote time of a peak point of the second pulse wave DC component signal in the contact pressure decreasing period; T9 may denote time of a valley point of a differentiated first pulse wave DC component signal in the contact pressure increasing period; T10 may denote time of a valley point of the differentiated second pulse wave DC component signal in the contact pressure increasing period; T11 may denote time of a peak point of the differentiated first pulse wave DC component signal in the contact pressure decreasing period; T12 may denote time of a peak point of the differentiated second pulse wave DC component signal in the contact pressure decreasing period; T13 may denote time of a peak point of a first pulse wave AC component signal in a contact pressure increasing period; T14 may denote time of a peak point of the second pulse wave AC component signal in the contact pressure increasing period; T15 may denote time of a valley point of a first pulse wave AC component signal in a contact pressure decreasing period; T16 may denote time of a valley point of the second pulse wave AC component signal in a contact pressure decreasing period; T17 may denote time of a peak point of a DC component differential signal in the contact pressure increasing period; T18 may denote time of a valley point of the DC component differential signal in the contact pressure increasing period; T19 may denote time of a peak point of a differentiated DC component differential signal in the contact pressure increasing period; T20 may denote time of a valley point of the DC component differential signal in the contact pressure decreasing period; T21 may denote time of a peak point of a DC component differential signal in the contact pressure decreasing period; T22 may denote time of a valley point of the differentiated DC component differential signal in the contact pressure decreasing period; T23 may denote time when the contract pressure starts to increase; T24 may denote time when the contract pressure starts to decrease; A1 may denote an amplitude of the first pulse wave DC component signal at T1; A2 may denote an amplitude of the first pulse wave DC component signal at T2; A3 may denote an amplitude of the second pulse wave DC component signal at T3; A4 may denote an amplitude of the second pulse wave DC component signal at T4; A5 may denote an amplitude of the first pulse wave DC component signal at T5; A6 may denote an amplitude of the first pulse wave DC component signal at T6; A7 may denote an amplitude of the second pulse wave DC component signal at T7; A8 may denote an amplitude of the second pulse wave DC component signal at T8; A9 may denote an amplitude of the differentiated first pulse wave DC component signal at T9; A10 may denote an amplitude of the differentiated second pulse wave DC component signal T10; A11 may denote an amplitude of the differentiated first pulse wave DC component signal T11; A12 may denote an amplitude of the differentiated second pulse wave DC component signal T12; A13 may denote an amplitude of the first pulse wave AC component signal T13; A14 may denote an amplitude of the second pulse wave AC component signal at T14; A15 may denote an amplitude of the first pulse wave AC component signal at T15; A16 may denote an amplitude of the second pulse wave AC component signal at T16; A17 may denote an amplitude of the DC component differential signal at T17; A18 may denote an amplitude of the DC component differential signal at T18; A19 may denote an amplitude of the differentiated DC component differential signal at T19; A20 may denote an amplitude of the DC component differential signal at T20; A21 may denote an amplitude of the DC component differential signal at T21; A22 may denote an amplitude of the differentiated DC component differential signal at T22; P1 may denote a contact pressure magnitude at T1; P2 may denote a contact pressure magnitude at T2; P3 may denote a contact pressure magnitude at T3; P4 may denote a contact pressure magnitude at T4; P5 may denote a contact pressure magnitude at T5; P6 may denote a contact pressure magnitude at T6; P7 may denote a contact pressure magnitude at T7; P8 may denote a contact pressure magnitude at T8; P9 may denote a contact pressure magnitude at T9; P10 may denote a contact pressure magnitude at T10; P11 may denote a contact pressure magnitude at T11; P12 may denote a contact pressure magnitude at T12; P13 may denote a contact pressure magnitude at T13; P14 may denote a contact pressure magnitude at T14; P15 may denote a contact pressure magnitude at T15; P16 may denote a contact pressure magnitude at T16; P17 may denote a contact pressure magnitude at T17; P18 may denote a contact pressure magnitude at T18; P19 may denote a contact pressure magnitude at T19; P20 may denote a contact pressure magnitude at T20; P21 may denote a contact pressure magnitude at T21; P22 may denote a contact pressure magnitude at T22; P23 may denote a contact pressure magnitude at T23; P24 may denote a contact pressure magnitude at T24; Pgmax may denote a maximum value of a contact pressure gradient in the contact pressure increasing period; and Pgmin may denote a minimum value of a contact pressure gradient in the contact pressure decreasing period.

The cardiovascular information may include at least one of blood pressure, vascular age, arterial stiffness, cardiac output, vascular compliance, blood glucose, blood triglycerides, and peripheral vascular resistance.

The object may be a user of the pulse wave measure, and the method of estimating cardiovascular information may further include generating and outputting guide information about an action of the user for estimating the cardiovascular information.

The method of estimating cardiovascular information may further include controlling the contact pressure between the object and the pulse wave measurer.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
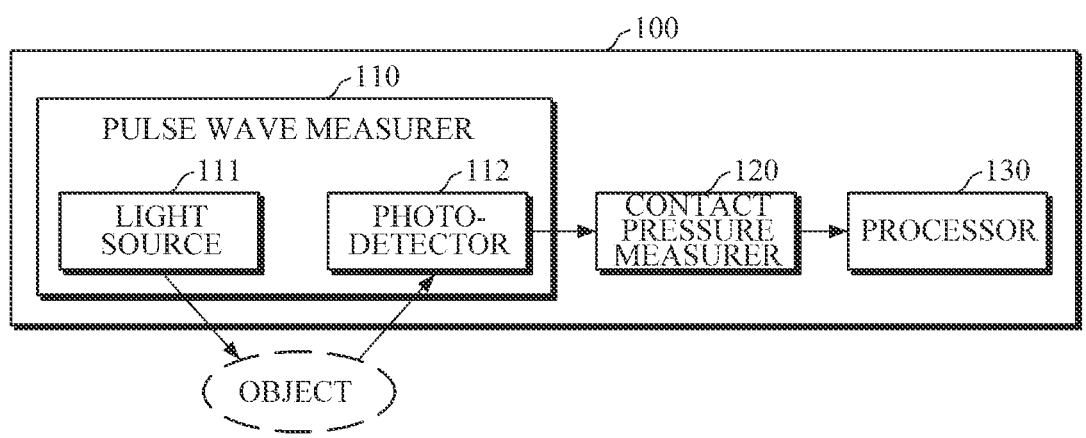
FIG. 1 is a block diagram illustrating an apparatus for estimating cardiovascular information according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Process steps described herein may be performed differently from a specified order, unless a specified order is clearly stated in the context of the disclosure. That is, each step may be performed in a specified order, at substantially the same time, or in a reverse order.

It will be understood that, although the terms first, second, etc. may be used herein to describe various elements, these elements should not be limited by these terms. These terms are only used to distinguish one element from another. Any references to singular may include plural unless expressly stated otherwise. In the present specification, it should be understood that the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Further, components that will be described in the specification are discriminated merely according to functions mainly performed by the components. That is, two or more components which will be described later can be integrated into a single component. Furthermore, a single component which will be explained later can be separated into two or more components. Moreover, each component which will be described can additionally perform some or all of a function executed by another component in addition to the main function thereof. Some or all of the main function of each component which will be explained can be carried out by another component. Each component may be implemented in hardware or software, or a combination thereof.

FIG. 1 is a block diagram illustrating an apparatus for estimating cardiovascular information according to an exemplary embodiment. The apparatus 100 for estimating cardiovascular information may be embedded in an electronic device. In particular, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the examples of the electronic device and the wearable device are not limited thereto.

Referring to FIG. 1, the apparatus 100 for estimating cardiovascular information includes a pulse wave measurer 110, a contact pressure measurer 120, and a processor 130.

The pulse wave measurer 110 may measure a first pulse wave signal and a second pulse wave signal from an object by using light of different wavelengths. To this end, the pulse wave measurer 110 includes a light source 111 may emit light of different wavelengths onto an object. The first pulse wave signal and the second pulse wave signal may have a first wavelength band and a second wavelength band, respectively, which are different from each other. The first wavelength band may partially overlap with the second wavelength band, or may be separated from the second wavelength band.

The light source 111 may emit light of different wavelengths. For example, the light source 111 may emit visible light or infrared light onto an object. However, wavelengths of light emitted by the light source 111 may vary according to a purpose of measurement and the like. Further, the light source 111 may include a single light emitting body, or an array of a plurality of light emitting bodies. In the case where the light source 111 is configured as an array of a plurality of light emitting bodies, the plurality of light emitting bodies may emit light of different wavelengths according to the purpose of measurement, or all the light emitting bodies may emit light of the same wavelength. In one exemplary embodiment, the light source 111 may include a light emitting diode (LED), a laser diode, or the like. However, this is merely exemplary, and the light source 111 is not limited thereto Further, the light source 111 may further include at least one optical element for directing the emitted light toward a desired position of an object.

The photodetector 112 may measure a pulse wave signal by receiving light reflected or scattered from the object. In one exemplary embodiment, the photodetector 112 may include a photo diode, a photo transistor (PTr), a charge-coupled device (CCD), and the like. The photodetector 112 may be formed as a single device, or an array of a plurality of devices.

The contact pressure measurer 120 may measure contact pressure between the object and the pulse wave measurer 110. In one exemplary embodiment, the contact pressure measurer 120 may measure contact pressure between the object and the pulse wave measurer 1110 by using a force sensor, a pressure sensor, an acceleration sensor, a piezoelectric film, a load cell, radar, a photoplethysmography (PPG) sensor, and the like.

The processor 130 may extract cardiovascular characteristic values based on the first pulse wave signal, the second pulse wave signal, and the contact pressure, and may estimate cardiovascular information based on the extracted cardiovascular characteristic values. For example, the processor 130 may extract at least one pulse wave feature point based on the first pulse wave signal and the second pulse wave signal in a contact pressure increasing period or a contact pressure decreasing period, and may extract cardiovascular characteristic values by using a pulse wave characteristic value, a contact pressure value, and the like which correspond to the extracted at least one pulse wave feature point. Further, the processor 130 may estimate cardiovascular information based on the extracted cardiovascular characteristic values. In this case, the cardiovascular characteristics may refer to characteristics associated with cardiovascular information desired to be estimated, and the cardiovascular information may include blood pressure, vascular age, arterial stiffness, cardiac output, vascular compliance, blood glucose, blood triglycerides, peripheral vascular resistance, and the like.

Hereinafter, the processor will be described in detail with reference to FIG. 2.

Figure 2:
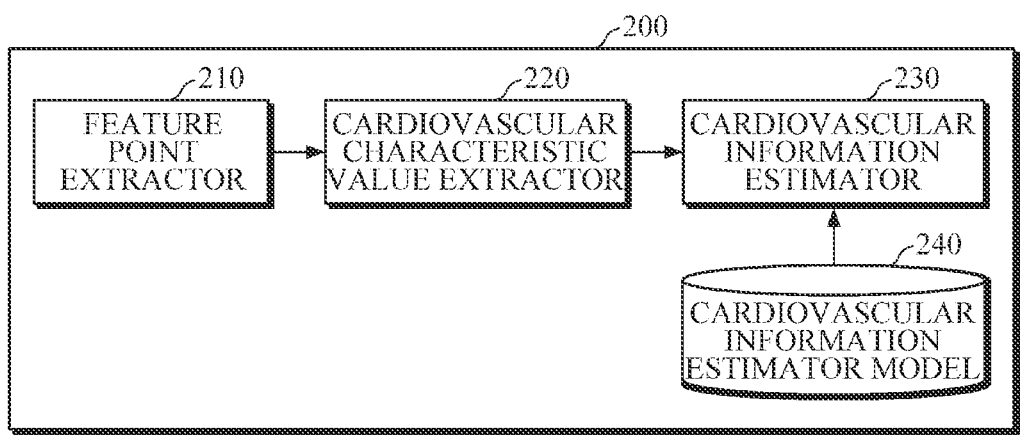
FIG. 2 is a block diagram illustrating a processor according to an exemplary embodiment.

FIG. 2 is a block diagram illustrating a processor according to an exemplary embodiment. The processor 200 of FIG. 2 may be an example of the processor 130 of FIG. 1.

Referring to FIG. 2, the processor 200 includes a feature point extractor 210, a cardiovascular characteristic value extractor 220, a cardiovascular information estimator 230, and a cardiovascular information estimation model 240. In FIG. 2, the cardiovascular information estimation model 240 is illustrated as part of the processor 100, but the present exemplary embodiment is not limited thereto. For example, the cardiovascular information estimation model 240 may be stored on a storage separately provided from the processor 100.

The feature point extractor 210 may detect a contact pressure increasing period or a contact pressure decreasing period based on a measured contact pressure value. The contact pressure increasing period and the contact pressure decreasing period may be referred to as a contact pressure transition period. The feature point extractor 210 may extract at least one pulse wave feature point based on a first pulse wave signal and a second pulse wave signal in the contact pressure transition period. In one exemplary embodiment, the feature point extractor 210 may extract, as pulse wave feature points, a valley point and a peak point of a direct current (DC) component signal of the first pulse wave signal in the contact pressure transition period (hereinafter referred to as a first pulse wave DC component signal), a valley point and a peak point of a DC component signal of the second pulse wave signal in the contact pressure transition period (hereinafter referred to as a second pulse wave DC component signal), a valley point and a peak point of a signal generated by differentiating the first pulse wave DC component signal in the contact pressure transition period (hereinafter referred to as a differentiated first pulse wave DC component signal), a valley point and a peak point of a signal generated by differentiating the second pulse wave DC component signal in the contact pressure transition period (hereinafter referred to as a differentiated second pulse wave DC component signal), a valley point and a peak point of an alternating current (AC) component signal of the first pulse wave signal in the contact pressure transition period (hereinafter referred to as a first pulse wave AC component signal), a valley point and a peak point of an AC component signal of the second pulse wave signal in the contact pressure transition period (hereinafter referred to as a second pulse wave AC component signal), a valley point and a peak point of a differential signal of the first pulse wave DC component signal and the second pulse wave DC component signal in the contact pressure transition period (hereinafter referred to as a DC component differential signal), a valley point and a peak point of a signal generated by differentiating the DC component differential signal in the contact pressure transition period (hereinafter referred to as a differentiated DC component differential signal), and the like.

The cardiovascular characteristic value extractor 220 may extract cardiovascular characteristic values based on the extracted at least one pulse wave feature point.

In one exemplary embodiment, the cardiovascular characteristic value extractor 220 may extract cardiovascular characteristic values by using a pulse wave characteristic value and/or a contact pressure value which correspond to the extracted at least one pulse wave feature point. For example, the cardiovascular characteristic value extractor 220 may extract cardiovascular characteristic values by linearly or non-linearly combining at least one or two or more of T1, T2, T3, T4, T5, T6, T7, T8, T9, T10, T11, T12, T13, T14, T15, T16, T17, T18, T19, T20, T21, T22, T23, T24, A1, A2, A3, A4, A5, A6, A7, A8, A9, A10, A11, A12, A13, A14, A15, A16, A17, A18, A19, A20, A21, A22, P1, P2, P3, P4, P5, P6, P7, P8, P9, P10, P11, P12, P13, P14, P15, P16, P17, P18, P19, P20, P21, P22, P23, P24, Pgmax, and Pgmin. Here, T1 denotes time of a valley point of a first pulse wave DC component signal in a contact pressure increasing period; T2 denotes time of a peak point of a first pulse wave DC component signal in a contact pressure increasing period; T3 denotes time of a valley point of a second pulse wave DC component signal in a contact pressure increasing period; T4 denotes time of a peak point of a second pulse wave DC component signal in a contact pressure increasing period; T5 denotes time of a valley point of a first pulse wave DC component signal in a contact pressure decreasing period; T6 denotes time of a peak point of a first pulse wave DC component signal in a contact pressure decreasing period; T7 denotes time of a valley point of a second pulse wave DC component signal in a contact pressure decreasing period; T8 denotes time of a peak point of a second pulse wave DC component signal in a contact pressure decreasing period; T9 denotes time of a valley point of a differentiated first pulse wave DC component signal in a contact pressure increasing period; T10 denotes time of a valley point of a differentiated second pulse wave DC component signal in a contact pressure increasing period; T11 denotes time of a peak point of a differentiated first pulse wave DC component signal in a contact pressure decreasing period; T12 denotes time of a peak point of a differentiated second pulse wave DC component signal in a contact pressure decreasing period; T13 denotes time of a peak point of a first pulse wave AC component signal in a contact pressure increasing period; T14 denotes time of a peak point of a second pulse wave AC component signal in a contact pressure increasing period; T15 denotes time of a valley point of a first pulse wave AC component signal in a contact pressure decreasing period; T16 denotes time of a valley point of a second pulse wave AC component signal in a contact pressure decreasing period; T17 denotes time of a peak point of a DC component differential signal in a contact pressure increasing period; T18 denotes time of a valley point of a DC component differential signal in a contact pressure increasing period; T19 denotes time of a peak point of a differentiated DC component differential signal in a contact pressure increasing period; T20 denotes time of a valley point of a DC component differential signal in a contact pressure decreasing period; T21 denotes time of a peak point of a DC component differential signal in a contact pressure decreasing period; T22 denotes time of a valley point of a differentiated DC component differential signal in a contact pressure decreasing period; T23 denotes time when contract pressure starts to increase; T24 denotes time when contract pressure starts to decrease; A1 denotes an amplitude of the first pulse wave DC component signal at T1; A2 denotes an amplitude of the first pulse wave DC component signal at T2; A3 denotes an amplitude of the second pulse wave DC component signal at T3; A4 denotes an amplitude of the second pulse wave DC component signal at T4; A5 denotes an amplitude of the first pulse wave DC component signal at T5; A6 denotes an amplitude of the first pulse wave DC component signal at T6; A7 denotes an amplitude of the second pulse wave DC component signal at T7; A8 denotes an amplitude of the second pulse wave DC component signal at T8; A9 denotes an amplitude of the differentiated first pulse wave DC component signal at T9; A10 denotes an amplitude of the differentiated second pulse wave DC component signal T10; A11 denotes an amplitude of the differentiated first pulse wave DC component signal T11; A12 denotes an amplitude of the differentiated second pulse wave DC component signal T12; A13 denotes an amplitude of the first pulse wave AC component signal T13; A14 denotes an amplitude of the second pulse wave AC component signal at T14; A15 denotes an amplitude of the first pulse wave AC component signal at T15; A16 denotes an amplitude of the second pulse wave AC component signal at T16; A17 denotes an amplitude of the DC component differential signal at T17; A18 denotes an amplitude of the DC component differential signal at T18; A19 denotes an amplitude of the differentiated DC component differential signal at T19; A20 denotes an amplitude of the DC component differential signal at T20; A21 denotes an amplitude of the DC component differential signal at T21; A22 denotes an amplitude of the differentiated DC component differential signal at T22; P1 denotes a contact pressure magnitude at T1; P2 denotes a contact pressure magnitude at T2; P3 denotes a contact pressure magnitude at T3; P4 denotes a contact pressure magnitude at T4; P5 denotes a contact pressure magnitude at T5; P6 denotes a contact pressure magnitude at T6; P7 denotes a contact pressure magnitude at T7; P8 denotes a contact pressure magnitude at T8; P9 denotes a contact pressure magnitude at T9; P10 denotes a contact pressure magnitude at T10; P11 denotes a contact pressure magnitude at T11; P12 denotes a contact pressure magnitude at T12; P13 denotes a contact pressure magnitude at T13; P14 denotes a contact pressure magnitude at T14; P15 denotes a contact pressure magnitude at T15; P16 denotes a contact pressure magnitude at T16; P17 denotes a contact pressure magnitude at T17; P18 denotes a contact pressure magnitude at T18; P19 denotes a contact pressure magnitude at T19; P20 denotes a contact pressure magnitude at T20; P21 denotes a contact pressure magnitude at T21; P22 denotes a contact pressure magnitude at T22; P23 denotes a contact pressure magnitude at T23; P24 denotes a contact pressure magnitude at T24; Pgmax denotes a maximum value of a contact pressure gradient in the contact pressure increasing period; and Pgmin denotes a minimum value of a contact pressure gradient in the contact pressure decreasing period.

The cardiovascular information estimator 230 may estimate cardiovascular information of an object based on the extracted cardiovascular characteristic values. In particular, the cardiovascular information may include blood pressure, vascular age, arterial stiffness, cardiac output, vascular compliance, blood glucose, blood triglycerides, peripheral vascular resistance, and the like.

In one exemplary embodiment, the cardiovascular information estimator 230 may estimate cardiovascular information by using the cardiovascular information estimation model 240 which represents a correlation between cardiovascular characteristic values and cardiovascular information. For example, the cardiovascular information estimation model 240 may be generated in the form of a mathematical algorithm, a table, and the like, and may be stored in an internal or external database of the processor 200.

Hereinafter, various examples of pulse wave feature points and cardiovascular characteristic values will be described with reference to FIGS. 3 to 9.

Figure 3:
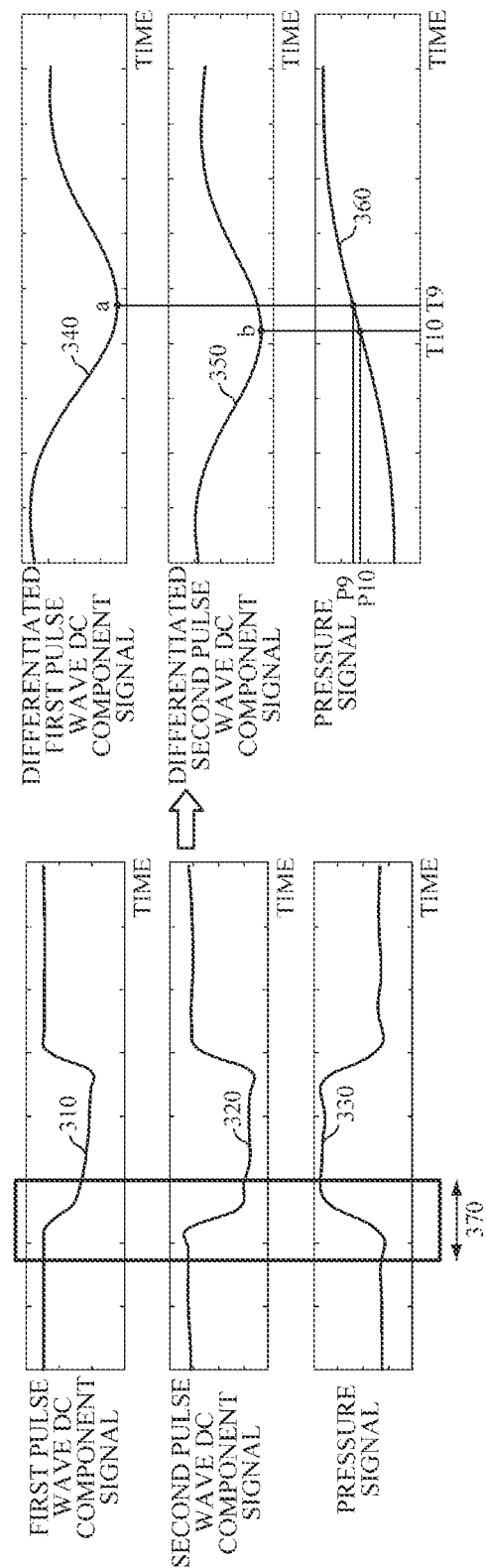
FIG. 3 is a diagram illustrating pulse wave feature points and cardiovascular characteristic values according to an exemplary embodiment.

FIG. 3 is a diagram illustrating pulse wave feature points and cardiovascular characteristic values according to an exemplary embodiment. In FIG. 3, reference numeral 310 refers to a first pulse wave DC component signal; reference numeral 320 refers to a second pulse wave DC component signal; reference numeral 330 refers to a contact pressure signal; reference numeral 340 refers to a differentiated first pulse wave DC component signal in a contact pressure increasing period 370; reference numeral 350 refers to a differentiated second pulse wave DC component signal in the contact pressure increasing period 370; and reference numeral 360 refers to a contact pressure signal in the contact pressure increasing period 370, which is time-aligned with the differentiated first pulse wave DC component signal 340 and the differentiated second pulse wave DC component signal 350. Further, the first pulse wave signal and the second pulse wave signal may be signals measured while contact pressure between an object and the pulse wave measurer increases and then decreases (e.g., during a period of time when a user touches the pulse wave measurer with a finger and then takes the finger off the pulse wave measurer).

Referring to FIGS. 2 and 3, the feature point extractor 210 may generate the first pulse wave DC component signal 310 and the second pulse wave DC component signal 320 by applying a low pass filter to the first pulse wave signal and the second pulse wave signal. Further, the feature point extractor 210 may detect the contact pressure increasing period 370 based on the measured contact pressure 330, and may generate the differentiated first pulse wave DC component signal 340 and the differentiated second pulse wave DC component signal 350 by differentiating the first pulse wave DC component signal 310 and the second pulse wave DC component signal 320 in the contact pressure increasing period 370.

The feature point extractor 210 may extract, as pulse wave feature points, a valley point a of the differentiated first pulse wave DC component signal 340 and a valley point b of the differentiated second pulse wave DC component signal 350.

The cardiovascular characteristic value extractor 220 may extract the time T9 corresponding to the valley point a of the differentiated first pulse wave DC component signal 340 and the contact pressure P9 at the time T9, and the time T10 corresponding to the valley point b of the differentiated second pulse wave DC component signal 350 and the contact pressure P10 at the time T10, and may extract a value obtained by (P9−P10)/(T9−T10) or |P9−P10|/|T9−T10| as a cardiovascular characteristic value.

Figure 4:
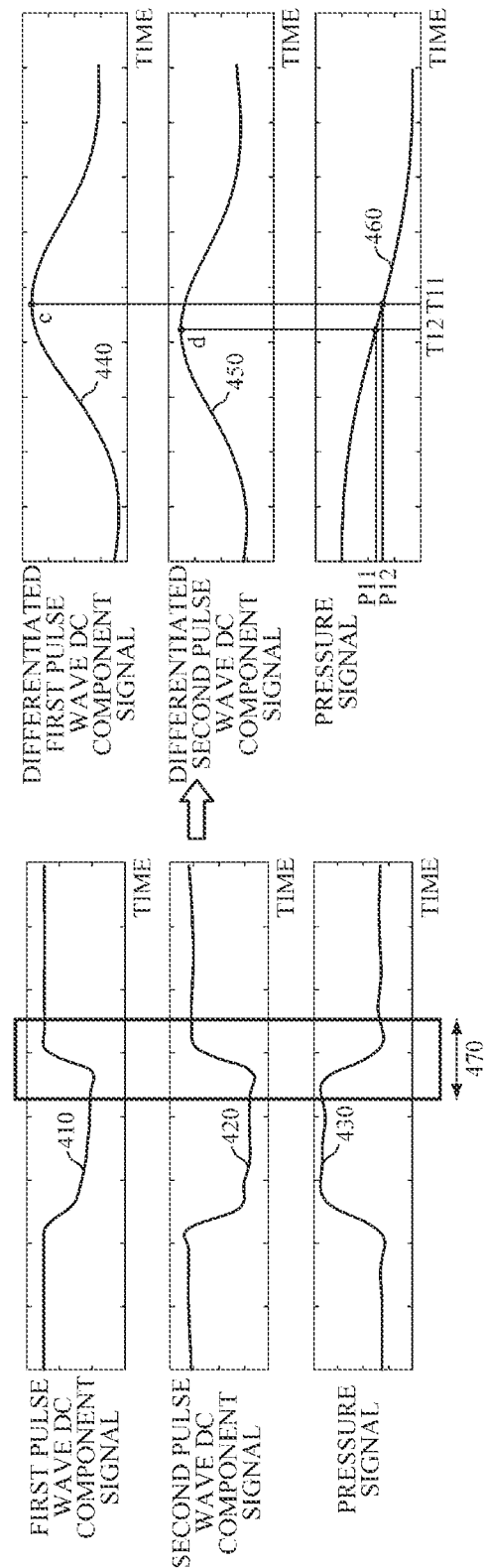
FIG. 4 is a diagram illustrating pulse wave feature points and cardiovascular characteristic values according to another exemplary embodiment.

FIG. 4 is a diagram illustrating pulse wave feature points and cardiovascular characteristic values according to another exemplary embodiment. In FIG. 4, reference numeral 410 refers to a first pulse wave DC component signal; reference numeral 420 refers to a second pulse wave DC component signal; reference numeral 430 refers to a contact pressure signal; reference numeral 440 refers to a differentiated first pulse wave DC component signal in a contact pressure decreasing period 470; reference numeral 450 refers to a differentiated second pulse wave DC component signal in the contact pressure decreasing period 470; and reference numeral 460 refers to a contact pressure signal in the contact pressure decreasing period 470, which is time-aligned with the differentiated first pulse wave DC component signal 440 and the differentiated second pulse wave DC component signal 450. Further, the first pulse wave signal and the second pulse wave signal may be signals measured while contact pressure between an object and the pulse wave measurer increases and then decreases (e.g., during a period of time when a user touches the pulse wave measurer with a finger and then takes the finger off the pulse wave measurer).

Referring to FIGS. 2 and 4, the feature point extractor 210 may generate the first pulse wave DC component signal 410 and the second pulse wave DC component signal 420 by applying a low pass filter to the first pulse wave signal and the second pulse wave signal. Further, the feature point extractor 210 may detect the contact pressure decreasing period 470 based on the measured contact pressure 430, and may generate the differentiated first pulse wave DC component signal 440 and the differentiated second pulse wave DC component signal 450 by differentiating the first pulse wave DC component signal 410 and the second pulse wave DC component signal 420 in the contact pressure decreasing period 470.

The feature point extractor 210 may extract, as pulse wave feature points, a peak point c of the differentiated first pulse wave DC component signal 440 and a peak point d of the differentiated second pulse wave DC component signal 450.

The cardiovascular characteristic value extractor 220 may extract the time T11 corresponding to the peak point c of the differentiated first pulse wave DC component signal 440 and the contact pressure P11 at the time T11, and the time T12 corresponding to the peak point d of the differentiated second pulse wave DC component signal 450 and the contact pressure P12 at the time T12, and may extract a value obtained by (P11−P12)/(T11−T12) or |P11−P12|/|T11−T12| as a cardiovascular characteristic value.

Figure 5:
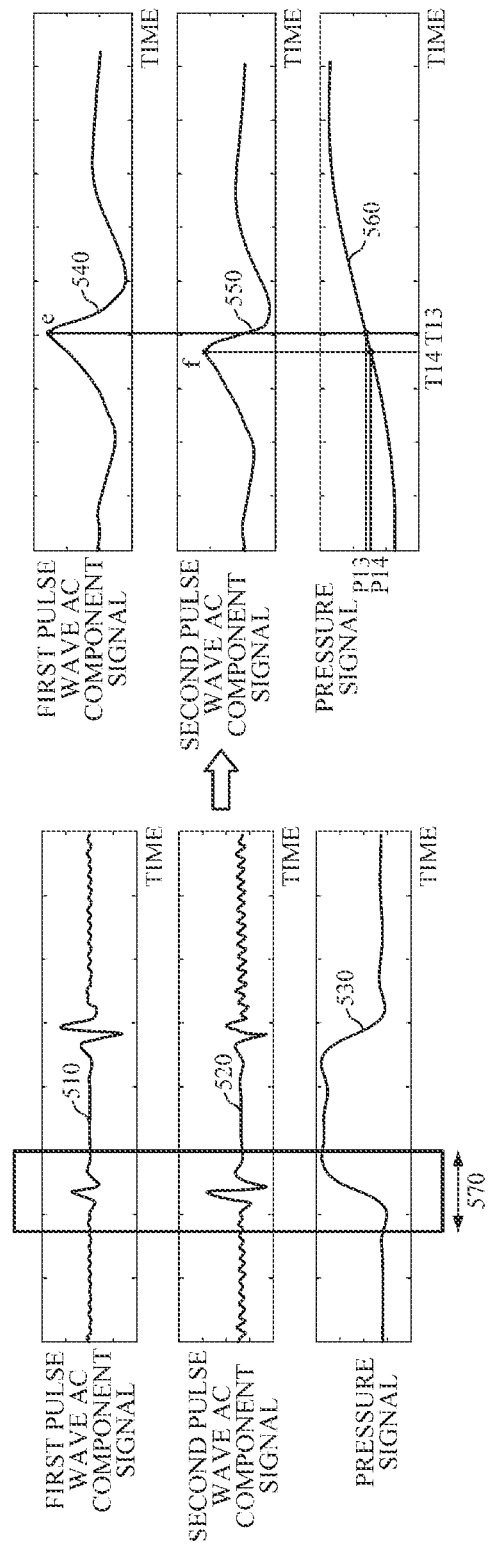
FIG. 5 is a diagram illustrating pulse wave feature points and cardiovascular characteristic values according to another exemplary embodiment.

FIG. 5 is a diagram illustrating pulse wave feature points and cardiovascular characteristic values according to another exemplary embodiment. In FIG. 5, reference numeral 510 refers to a first pulse wave AC component signal; reference numeral 520 refers to a second pulse wave AC component signal; reference numeral 530 refers to a contact pressure signal; reference numeral 540 refers to a first pulse wave AC component signal in a contact pressure increasing period 570; reference numeral 550 refers to a second pulse wave AC component signal in the contact pressure increasing period 570; and reference numeral 560 refers to a contact pressure signal in the contact pressure increasing period 570, which is time-aligned with the first pulse wave AC component signal 540 and the second pulse wave AC component signal 550. Further, the first pulse wave signal and the second pulse wave signal may be signals measured while contact pressure between an object and the pulse wave measurer increases and then decreases (e.g., during a period of time when a user touches the pulse wave measurer with a finger and then takes the finger off the pulse wave measurer).

Referring to FIGS. 2 and 5, the feature point extractor 210 may generate the first pulse wave AC component signal 510 and the second pulse wave AC component signal 520 by applying a band pass filter to the first pulse wave signal and the second pulse wave signal. Further, the feature point extractor 210 may detect the contact pressure increasing period 570 based on the measured contact pressure 530, and may extract the first pulse wave AC component signal 540 and the second pulse wave AC component signal 550 in the contact pressure increasing period 570.

The feature point extractor 210 may extract, as pulse wave feature points, a peak point e of the first pulse wave AC component signal 540 and a peak point f of the second pulse wave AC component signal 550.

The cardiovascular characteristic value extractor 220 may extract the time T13 corresponding to the peak point e of the first pulse wave AC component signal 540 and the contact pressure P13 at the time T13, and the time T14 corresponding to the peak point f of the second pulse wave AC component signal 550 and the contact pressure P14 at the time T14, and may extract a value obtained by (P13−P14)/(T13−T14) or |P13−P14|/|T13−T14| as a cardiovascular characteristic value.

Figure 6:
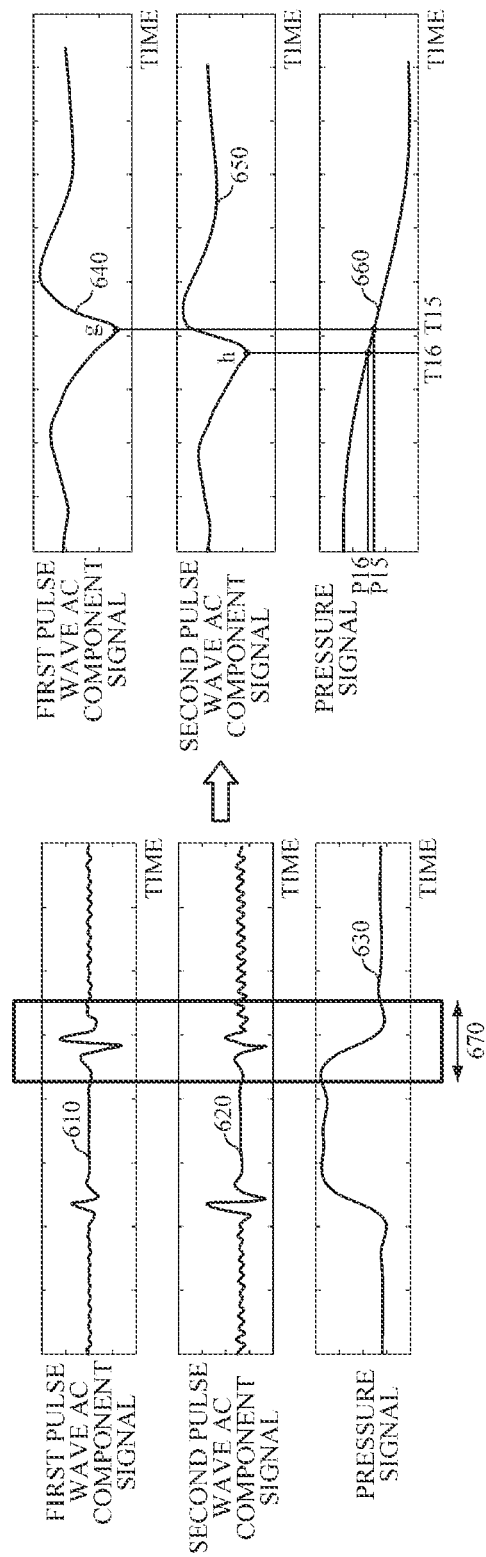
FIG. 6 is a diagram illustrating pulse wave feature points and cardiovascular characteristic values according to another exemplary embodiment.

FIG. 6 is a diagram illustrating pulse wave feature points and cardiovascular characteristic values according to another exemplary embodiment. In FIG. 6, reference numeral 610 refers to a first pulse wave AC component signal; reference numeral 620 refers to a second pulse wave AC component signal; reference numeral 630 refers to a contact pressure signal; reference numeral 640 refers to a first pulse wave AC component signal in a contact pressure decreasing period 670; reference numeral 650 refers to a second pulse wave AC component signal in the contact pressure decreasing period 670; and reference numeral 660 refers to a contact pressure signal in the contact pressure decreasing period 670, which is time-aligned with the first pulse wave AC component signal 640 and the second pulse wave AC component signal 650. Further, the first pulse wave signal and the second pulse wave signal may be signals measured while contact pressure between an object and the pulse wave measurer increases and then decreases (e.g., during a period of time when a user touches the pulse wave measurer with a finger and then takes the finger off the pulse wave measurer).

Referring to FIGS. 2 and 6, the feature point extractor 210 may generate the first pulse wave AC component signal 610 and the second pulse wave AC component signal 620 by applying a band pass filter to the first pulse wave signal and the second pulse wave signal. Further, the feature point extractor 210 may detect the contact pressure decreasing period 670 based on the measured contact pressure 630, and may extract the first pulse wave AC component signal 640 and the second pulse wave AC component signal 650 in the contact pressure decreasing period 670.

The feature point extractor 210 may extract, as pulse wave feature points, a valley point g of the first pulse wave AC component signal 640 and a valley point h of the second pulse wave AC component signal 650.

The cardiovascular characteristic value extractor 220 may extract the time T15 corresponding to the valley point g of the first pulse wave AC component signal 640 and the contact pressure P15 at the time T15, and the time T16 corresponding to the valley point h of the second pulse wave AC component signal 650 and the contact pressure P16 at the time T16, and may extract a value obtained by (P15−P16)/(T15−T16) or |P15−P16|/|T15−T16| as a cardiovascular characteristic value.

Figure 7:
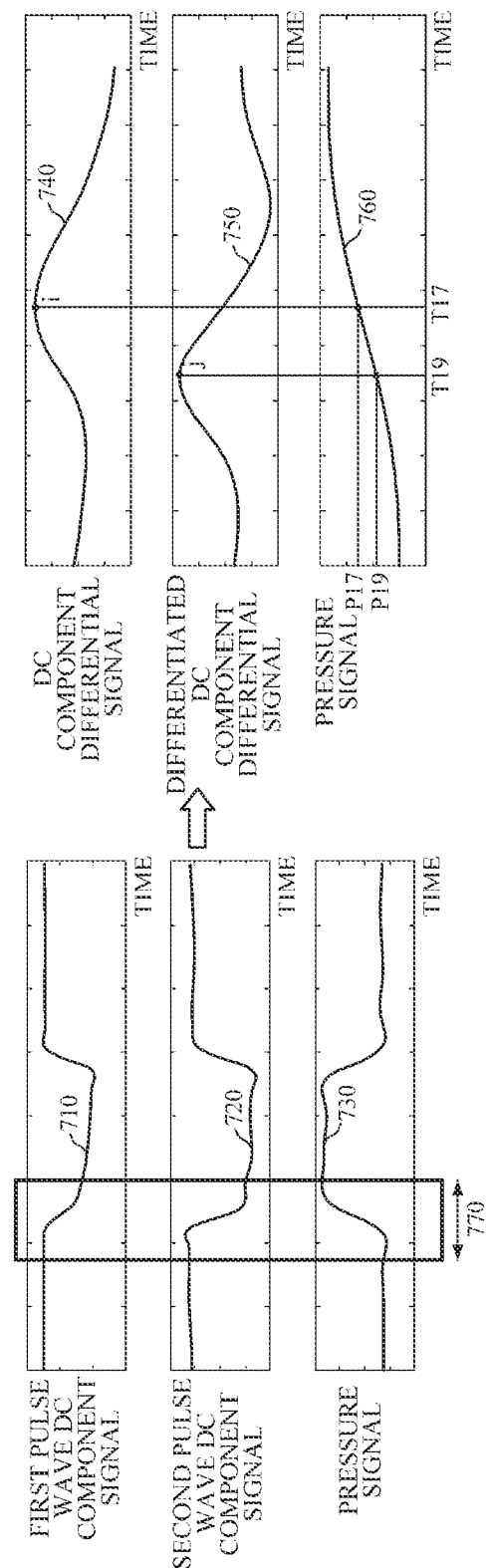
FIG. 7 is a diagram illustrating pulse wave feature points and cardiovascular characteristic values according to another exemplary embodiment.

FIG. 7 is a diagram illustrating pulse wave feature points and cardiovascular characteristic values according to another exemplary embodiment. In FIG. 7, reference numeral 710 refers to a first pulse wave DC component signal; reference numeral 720 refers to a second pulse wave DC component signal; reference numeral 730 refers to a contact pressure signal; reference numeral 740 refers to a DC component differential signal in a contact pressure increasing period 770; reference numeral 750 refers to a differentiated DC component differential signal in the contact pressure increasing period 770; and reference numeral 760 refers to a contact pressure signal in the contact pressure increasing period 770, which is time-aligned with the DC component differential signal 740 and the differentiated DC component differential signal 750. Further, the first pulse wave signal and the second pulse wave signal may be signals measured while contact pressure between an object and the pulse wave measurer increases and then decreases (e.g., during a period of time when a user touches the pulse wave measurer with a finger and then takes the finger off the pulse wave measurer).

Referring to FIGS. 2 and 7, the feature point extractor 210 may generate the first pulse wave DC component signal 710 and the second pulse wave DC component signal 720 by applying a low pass filter to the first pulse wave signal and the second pulse wave signal. Further, the feature point extractor 210 may generate the DC component differential signal 740 by subtracting the second pulse wave DC component signal 720 in the contact pressure increasing period 770 from the first pulse wave DC component signal 710 in the contact pressure increasing period 770, and may generate the differentiated DC component differential signal 750 by differentiating the DC component differential signal.

The feature point extractor 210 may extract, as pulse wave feature points, a peak point i of the DC component differential signal 740 and a peak point j of the differentiated DC component differential signal 750.

The cardiovascular characteristic value extractor 220 may extract the time T17 corresponding to the peak point i of the DC component differential signal 740 and the contact pressure P17 at the time T17, and the time T19 corresponding to the peak point j of the differentiated DC component differential signal 750 and the contact pressure P19 at the time T19, and may extract a value obtained by (P17−P19)/(T17−T19) or |P17−P19|/|T17−T19| as a cardiovascular characteristic value.

Figure 8:
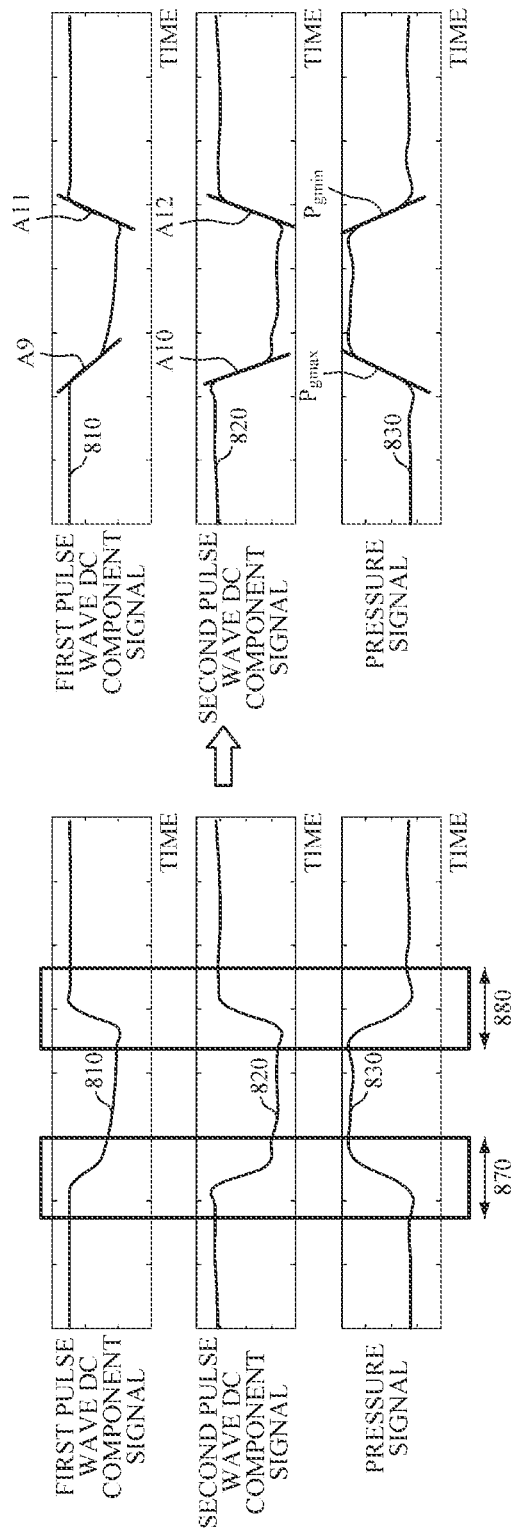
FIG. 8 is a diagram illustrating pulse wave feature points and cardiovascular characteristic values according to another exemplary embodiment.

FIG. 8 is a diagram illustrating pulse wave feature points and cardiovascular characteristic values according to another exemplary embodiment. In FIG. 8, reference numeral 810 refers to a first pulse wave DC component signal; reference numeral 820 refers to a second pulse wave DC component signal; and reference numeral 830 refers to a contact pressure signal. Further, the first pulse wave signal and the second pulse wave signal may be signals measured while contact pressure between an object and the pulse wave measurer increases and then decreases (e.g., during a period of time when a user touches the pulse wave measurer with a finger and then takes the finger off the pulse wave measurer).

Referring to FIGS. 2 and 8, the feature point extractor 210 may generate the first pulse wave DC component signal 810 and the second pulse wave DC component signal 820 by applying a low pass filter to the first pulse wave signal and the second pulse wave signal. Further, the feature point extractor 210 may detect a contact pressure increasing period 870 and a contact pressure decreasing period 880 based on the measured contact pressure 830. In addition, the feature point extractor 210 may extract, as pulse wave feature points, a point of maximum change of the first pulse wave DC component signal 810 and a point of maximum change of the second pulse wave DC component signal 820 in the contact pressure increasing period 870; and a point of maximum change of the first pulse wave DC component signal 810 and a point of maximum change of the second pulse wave DC component signal 820 in the contact pressure decreasing period 880. For example, the feature point extractor 210 may generate a differentiated first pulse wave DC component signal and a differentiated second pulse wave DC component signal in the contact pressure transition periods 870 and 880 by differentiating the first pulse wave DC component signal 810 and the second pulse wave DC component signal 820 in the contact pressure transition periods 870 and 880. Then, the feature point extractor 210 may extract, as pulse wave feature points, a valley point of the differentiated first pulse wave DC component signal and a valley point of the differentiated second pulse wave DC component signal in the contact pressure increasing period 870; and a peak point of the differentiated first pulse wave DC component signal and a peak point of the differentiated second pulse wave DC component signal in the contact pressure decreasing period 880.

The cardiovascular characteristic value extractor 220 may extract, as cardiovascular characteristic values, a gradient A9 at the point of the negative maximum change of the first pulse wave DC component signal 810 in the contact pressure increasing period 870 (amplitude of a valley point of the differentiated first pulse wave DC component signal in the contact pressure increasing period); a gradient A11 at the point of the positive maximum change of the first pulse wave DC component signal 810 in the contact pressure decreasing period 880 (amplitude of a peak point of the differentiated first pulse wave DC component signal in the contact pressure decreasing period); a gradient A10 at the point of the negative maximum change of the second pulse wave DC component signal 820 in the contact pressure increasing period 870 (amplitude of a valley point of the differentiated second pulse wave DC component signal in the contact pressure increasing period); a gradient A12 at the point of the positive maximum change of the second pulse wave DC component signal 820 in the contact pressure decreasing period 880 (amplitude of a peak point of the differentiated second pulse wave DC component signal in the contact pressure decreasing period); a gradient Pgmax of the point of the positive maximum change of contact pressure in the contact pressure increasing period 870; and a gradient Pgmin of the point of the negative maximum change of contact pressure in the contact pressure decreasing period 880. In addition, the cardiovascular characteristic value extractor 220 may extract a value obtained by (A9−A10)/Pgmax, (|A9|−|A10|)/Pgmax, |A9−A10|/Pgmax, or ||A9|−|A10||/Pgmax, as a cardiovascular characteristic value. Also, the cardiovascular characteristic value extractor 220 may extract a value obtained by (A11−A12)/Pgmin, (|A11|−|A12|)/Pgmin, |A11−A12|/Pgmin, or ||A11|−|A12||/Pgmin as a cardiovascular characteristic value.

Figure 9:
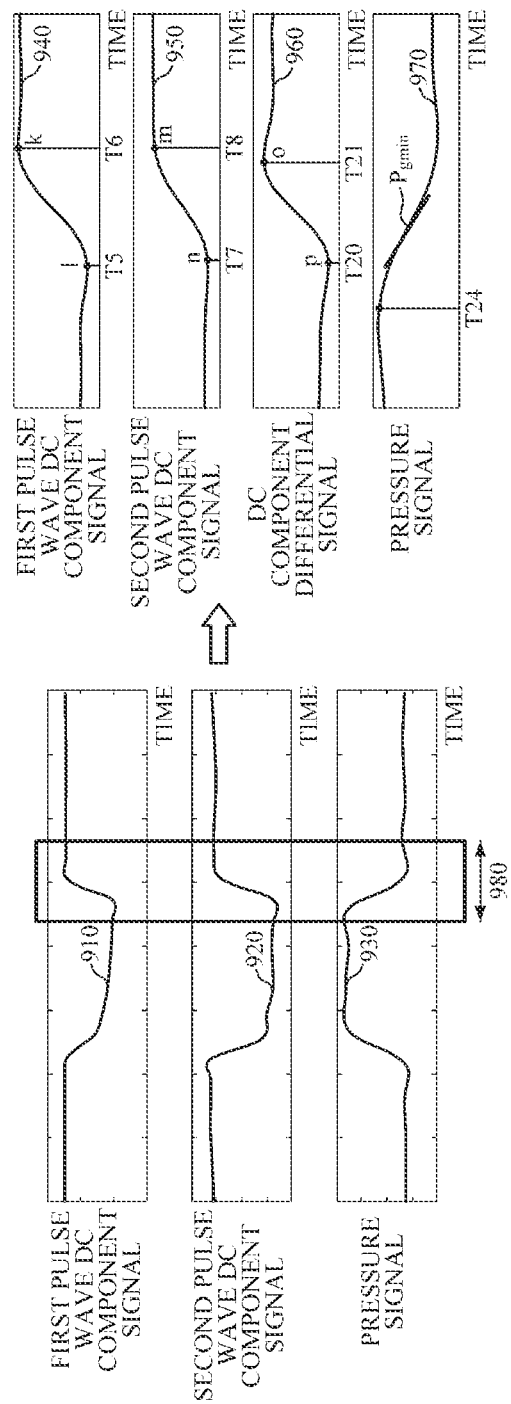
FIG. 9 is a diagram illustrating pulse wave feature points and cardiovascular characteristic values according to another exemplary embodiment.

FIG. 9 is a diagram illustrating pulse wave feature points and cardiovascular characteristic values according to another exemplary embodiment. In FIG. 9, reference numeral 910 refers to a first pulse wave DC component signal; reference numeral 920 refers to a second pulse wave DC component signal; reference numeral 930 refers to a contact pressure signal; reference numeral 940 refers to a first pulse wave DC component signal in a contact pressure decreasing period 980; reference numeral 950 refers to a second pulse wave DC component signal in the contact pressure decreasing period 980; and reference numeral 960 refers to a DC component differential signal in the contact pressure decreasing period 980; reference numeral 970 refers to a contact pressure signal in the contact pressure decreasing period 980, which is time-aligned with the first pulse wave DC component signal 940, the second pulse wave DC component signal 950, and the DC component differential signal 960. Further, the first pulse wave signal and the second pulse wave signal may be signals measured while contact pressure between an object and the pulse wave measurer increases and then decreases (e.g., during a period of time when a user touches the pulse wave measurer with a finger and then takes the finger off the pulse wave measurer).

Referring to FIGS. 2 and 9, the feature point extractor 210 may generate the first pulse wave DC component signal 910 and the second pulse wave DC component signal 920 by applying a low pass filter to the first pulse wave signal and the second pulse wave signal. Further, the feature point extractor 210 may detect a contact pressure decreasing period 980 based on the measured contact pressure 930; and may generate the DC component differential signal 960 by subtracting the second pulse wave DC component signal 950 in the contact pressure decreasing period 980 from the first pulse wave DC component signal 940 in the contact pressure decreasing period 980.

The feature point extractor 210 may extract, as pulse wave feature points, a peak point k and a valley point l of the first pulse wave DC component signal 940, a peak point m and a valley point n of the second pulse wave DC component signal 950, and a peak point o and a valley point p of the DC component differential signal 960.

The cardiovascular characteristic value extractor 220 may extract, as cardiovascular characteristic values: the time T6 corresponding to the peak point k of the first pulse wave DC component signal 940; the time T5 corresponding to the valley point l of the first pulse wave DC component signal 940; the time T8 corresponding to the peak point m of the second pulse wave DC component signal 950; the time T7 corresponding to the valley point n of the second pulse wave DC component signal 950; the time T21 corresponding to the peak point o of the DC component differential signal 960; the time T20 corresponding to the valley point p of the DC component differential signal 960; the time T24 when contact pressure starts to decrease; and the gradient Pgmin of a maximum change point of contact pressure in the contact pressure decreasing period 980. In addition, the cardiovascular characteristic value extractor 220 may extract a value obtained by (T6−T5)/Pgmin, a value obtained by (T8−T7)/Pgmin, a value obtained by (T21−T20)/Pgmin, a value obtained by (T6−T24)/Pgmin, a value obtained by (T8−T24)/Pgmin, a value obtained by (T21−T24)/Pgmin, and the like.

Figure 10:
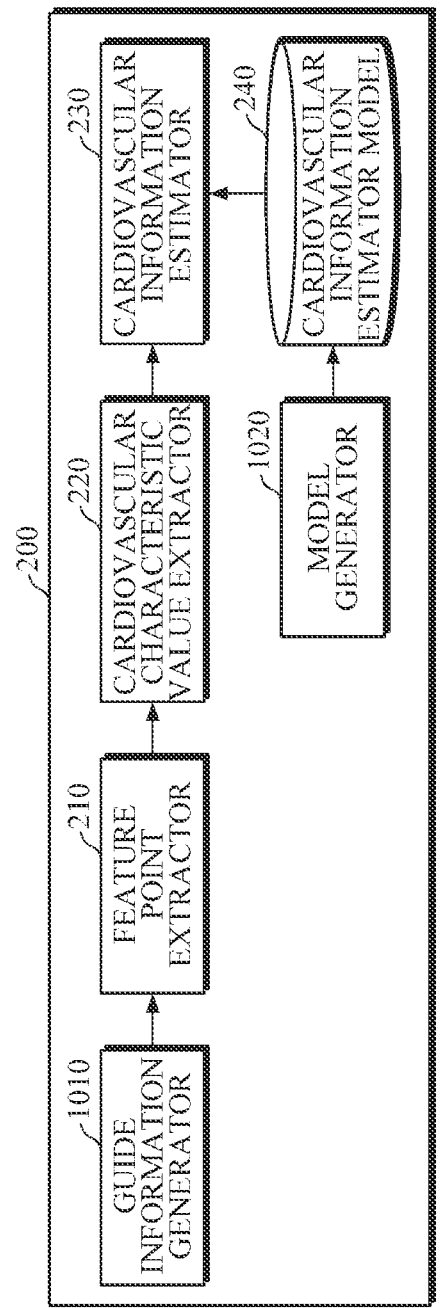
FIG. 10 is a block diagram illustrating a processor according to another exemplary embodiment.

FIG. 10 is a block diagram illustrating a processor according to another exemplary embodiment. The processor 1000 of FIG. 10 may be another example of the processor 130 of FIG. 1.

Referring to FIG. 10, the processor 100 includes a feature point extractor 210, a cardiovascular characteristic value extractor 220, a cardiovascular information estimator 230, a guide information generator 1010, and a model generator 1020. Here, the feature point extractor 210, the cardiovascular characteristic value extractor 220 and the cardiovascular information estimator 230 are described above with reference to FIG. 2, such that detailed description thereof will be omitted.

The guide information generator 1010 may generate guide information for guiding a user to increase or decrease contact pressure.

The model generator 1020 may generate a cardiovascular information estimation model 240 which represents a correlation between cardiovascular characteristic values and cardiovascular information. In particular, the cardiovascular information estimation model 240 may be generated in the form of a mathematical algorithm, a table, and the like, to estimate cardiovascular information from cardiovascular characteristic values. In FIG. 10, the cardiovascular information estimation model 240 is illustrated as being stored in the processor 200, but the present exemplary embodiment is not limited thereto. For example, the cardiovascular information estimation model 240 may be stored on a storage separately provided from the processor 200.

In one exemplary embodiment, the model generator 1020 may collect learning data associated with cardiovascular characteristic values and cardiovascular information corresponding thereto, and may generate the cardiovascular information estimation model by regression analysis or by machine learning using the collected learning data. In this case, examples of the regression analysis algorithm may include simple linear regression, multi linear regression, logistic regression, proportional Cox regression, and the like. Examples of the machine learning may include Artificial Neural Network, Decision Tree, Genetic Algorithm, Genetic Programming, K-Nearest Neighbor, Radial Basis Function Network, Random Forest, Support Vector Machine, deep-learning, and the like.

Figure 11:
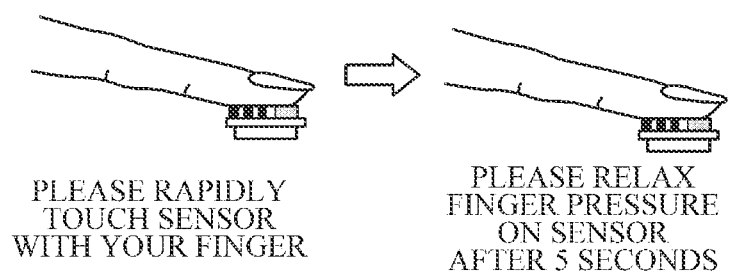
FIG. 11 is a diagram illustrating guide information according to an exemplary embodiment.

FIG. 11 is a diagram illustrating an example of guide information, which is generated when an apparatus for estimating cardiovascular information is embedded in a cellular phone, a smartphone, a tablet PC, a laptop computer, a personal digital assistant (PDA), a portable multimedia player (PMP), a navigation, an MP3 player, a digital camera, and the like.

Referring to FIG. 11, the guide information may prompt a user to perform the following two steps: a first step of increasing contact pressure between an object and a pulse wave measurer by rapidly touching a sensor with a finger; and a second step of decreasing the contact pressure between the object and the pulse wave measurer by rapidly relaxing the finger pressure on the sensor.

Figure 12:
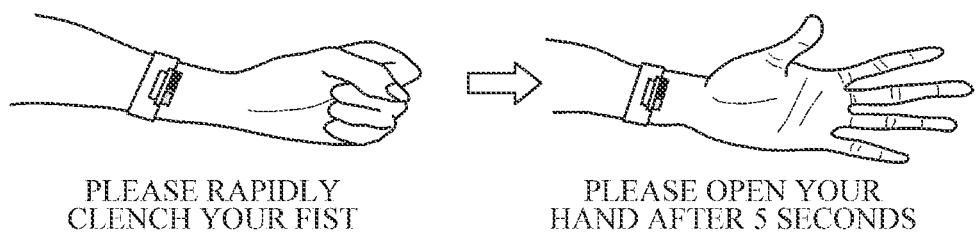
FIG. 12 is a diagram illustrating guide information according to another exemplary embodiment.

FIG. 12 is a diagram illustrating another example of guide information, which is generated when an apparatus for estimating cardiovascular information is embedded in a wrist-type wearable device.

Referring to FIG. 12, the guide information may prompt a user to perform the following two steps: a first step of increasing contact pressure between an object and a pulse wave measurer by rapidly clenching the fist while wearing the wrist-type wearable device; and a second step of decreasing contact pressure between the object and the pulse wave measurer by rapidly opening the hand after clenching the fist while wearing the wrist-type wearable device.

Figure 13:
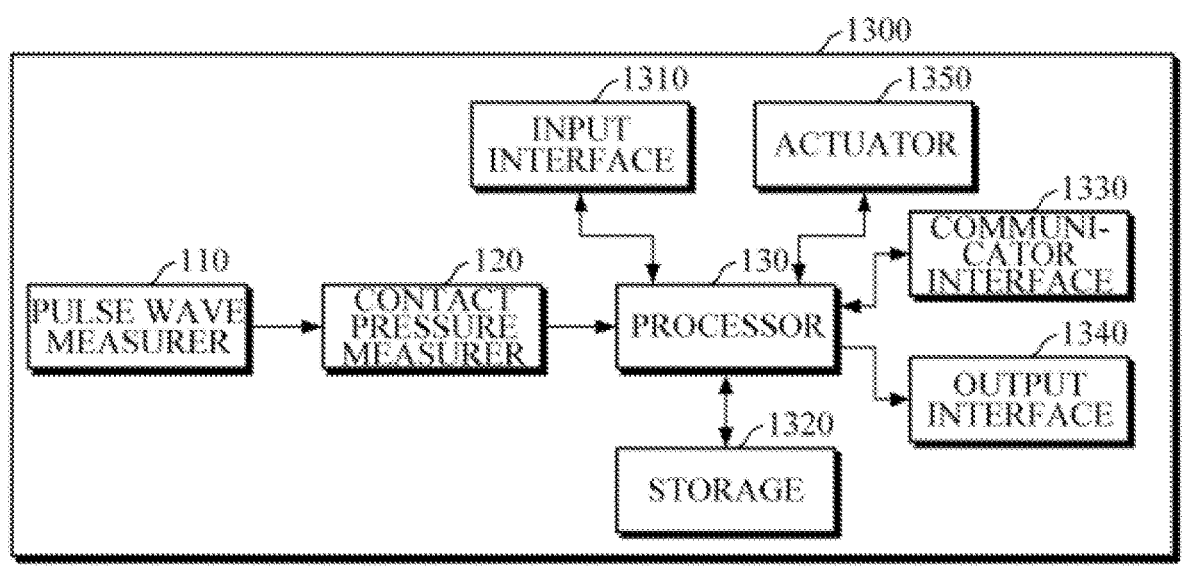
FIG. 13 is a block diagram illustrating an apparatus for estimating cardiovascular information according to another exemplary embodiment.

FIG. 13 is a block diagram illustrating another example of an apparatus for estimating cardiovascular information. The apparatus 1300 for estimating cardiovascular information of FIG. 13 may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 13, the apparatus 1300 for estimating cardiovascular information includes a pulse wave measurer 110, a contact pressure measurer 120, a processor 130, an input interface 1310, a storage interface 1320, a communication interface 1330, an output interface 1340, and an actuator 1350. Here, the pulse wave measurer 110, the contact pressure measurer 120, and the processor 130 are described above with reference to FIGS. 1 to 12, such that detailed description thereof will be omitted.

The input interface 1310 may receive input of various operation signals from a user. In one exemplary embodiment, the input interface 1310 may include a keypad, a dome switch, a touch pad (static pressure/capacitance), a jog wheel, a jog switch, a hardware (H/W) button, and the like. Particularly, the touch pad, which forms a layer structure with a display, may be called a touch screen.

The storage interface 1320 may store programs or commands for operation of the apparatus 1300 for estimating cardiovascular information, and may store data input to and output from the apparatus 1300 for estimating cardiovascular information. Further, the storage interface 1320 may store a first pulse wave signal and a second pulse wave signal which are measured by the pulse wave measurer 110, contact pressure measured by the contact pressure measurer 120, pulse wave feature points and cardiovascular characteristic values which are extracted by the processor 130, cardiovascular information estimated by the processor 130, guide information generated by the processor 130, a cardiovascular information estimation model, and the like.

The storage interface 1320 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 1300 for estimating cardiovascular information may operate an external storage medium, such as web storage and the like, which performs a storage function of the storage interface 1320 on the Internet.

The communication interface 1330 may perform communication with an external device. For example, the communication interface 1330 may transmit, to the external device, data input by a user through the input interface 1310, the first pulse wave signal and second pulse wave signal which are measured by the pulse wave measurer 110, the contact pressure measured by the contact pressure measurer 120, the pulse wave feature points and cardiovascular characteristic values which are extracted by the processor 130, the cardiovascular information estimated by the processor 130, the guide information generated by the processor 130, the cardiovascular information estimation model, and the like, or may receive, from the external device, various data useful for estimating cardiovascular information.

In particular, the external device may be medical equipment using the first pulse wave signal and second pulse wave signal which are measured by the pulse wave measurer 110, the contact pressure measured by the contact pressure measurer 120, the pulse wave feature points and cardiovascular characteristic values which are extracted by the processor 130, the cardiovascular information estimated by the processor 130, the guide information generated by the processor 130, the cardiovascular information estimation model, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 1330 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wide-band (UWB) communication, Ant+ communication, WIFI communication, Radio Frequency Identification (RFID) communication, 3G communication, 4G communication, 5G communication, and the like. However, this is merely exemplary and is not intended to be limiting.

The output interface 1340 may output the first pulse wave signal and second pulse wave signal which are measured by the pulse wave measurer 110, the contact pressure measured by the contact pressure measurer 120, the pulse wave feature points and cardiovascular characteristic values which are extracted by the processor 130, the cardiovascular information estimated by the processor 130, the guide information generated by the processor 130, the cardiovascular information estimation model, and the like. In one exemplary embodiment, the output interface 1340 may output the first pulse wave signal and second pulse wave signal which are measured by the pulse wave measurer 110, the contact pressure measured by the contact pressure measurer 120, the pulse wave feature points and cardiovascular characteristic values which are extracted by the processor 130, the cardiovascular information estimated by the processor 130, the guide information generated by the processor 130, the cardiovascular information estimation model, and the like, by using at least one of an acoustic method, a visual method, and a tactile method. To this end, the output interface 1340 may include a display, a speaker, a vibrator, and the like.

The actuator 1350 may control contact pressure between an object and the pulse wave measurer 110. For example, the actuator 1350 may increase the contact pressure between the object and the pulse wave measurer 110 to a predetermined level, and after maintaining the contact pressure at the level for a predetermined period of time, the actuator 1350 may decrease the contact pressure.

Figure 14:
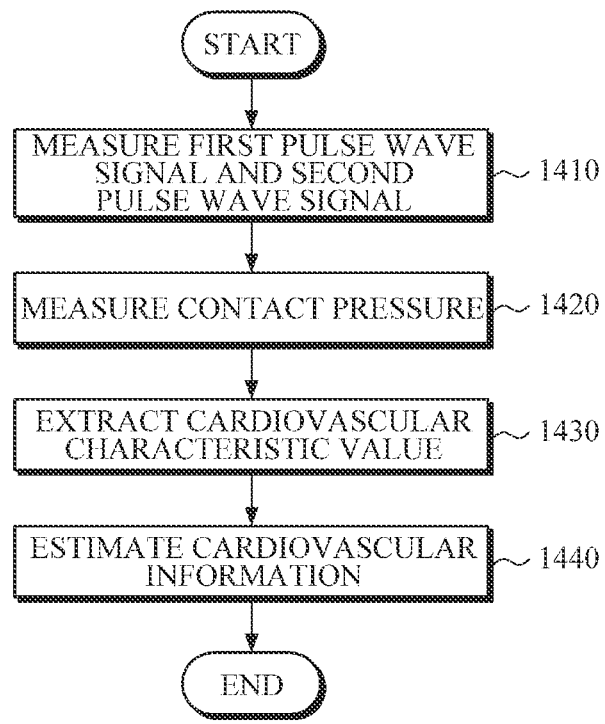
FIG. 14 is a flowchart illustrating a method of estimating cardiovascular information according to an exemplary embodiment.

FIG. 14 is a flowchart illustrating an example of a method of estimating cardiovascular information. The method of estimating cardiovascular information of FIG. 14 may be performed by the apparatus 100 for estimating cardiovascular information of FIG. 1.

Referring to FIGS. 1 and 14, the apparatus 100 for estimating cardiovascular information may measure a first pulse wave signal and a second pulse wave signal by using light of different wavelengths in operation 1410. For example, the apparatus 100 for estimating cardiovascular information may emit light of different wavelengths onto an object, and may measure the first pulse wave signal and the second pulse wave signal by receiving light reflected or scattered from the object. The first pulse wave signal and the second pulse wave signal may have a first wavelength band and a second wavelength band, respectively, which are different from each other. The first wavelength band may partially overlap with the second wavelength band, or may be separated from the second wavelength band.

The apparatus 100 for estimating cardiovascular information may measure contact pressure between the object and the pulse wave measurer in operation 1420. In one exemplary embodiment, the apparatus 100 for estimating cardiovascular information may measure contact pressure between the object and the pulse wave measurer by using a force sensor, a pressure sensor, an acceleration sensor, a piezoelectric film, a load cell, radar, a photoplethysmography (PPG) sensor, and the like.

The apparatus 100 for estimating cardiovascular information may extract cardiovascular characteristic values based on the first pulse wave signal, the second pulse wave signal, and the contact pressure in operation 1430, and may estimate cardiovascular information based on the extracted cardiovascular characteristic values in operation 1440. In this case, the cardiovascular characteristics may refer to characteristics associated with cardiovascular information desired to be estimated, and the cardiovascular information may include blood pressure, vascular age, arterial stiffness, cardiac output, vascular compliance, blood glucose, blood triglycerides, peripheral vascular resistance, and the like.

Figure 15:
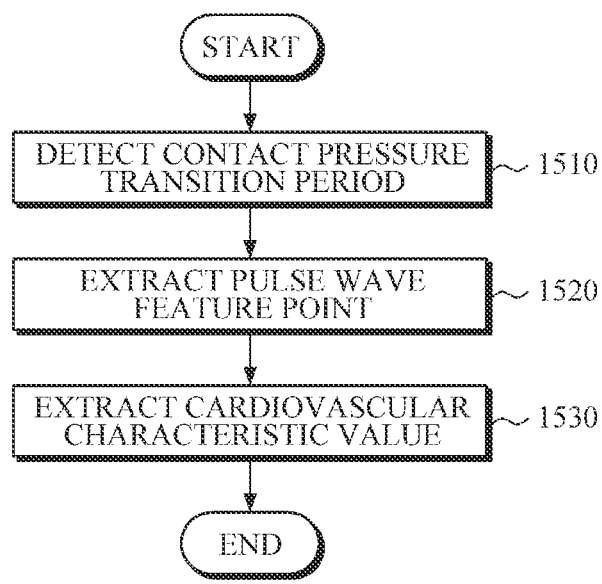
FIG. 15 is a flowchart illustrating a method of extracting cardiovascular characteristic values according to an exemplary embodiment.

FIG. 15 is a flowchart illustrating a method of extracting cardiovascular characteristic values according to an exemplary embodiment. The method of extracting cardiovascular characteristic values may be an example of the method of extracting cardiovascular characteristic values in 1430 of FIG. 14.

Referring to FIGS. 1 and 15, the apparatus 100 for estimating cardiovascular information may detect a contact pressure transition period based on contact pressure in operation 1510. The contact pressure transition period may include a contact pressure increasing period and a contact pressure decreasing period.

The apparatus 100 for estimating cardiovascular information may extract at least one pulse wave feature point based on the first pulse wave signal and the second pulse wave signal in the contact pressure transition period in operation 1520. For example, the apparatus 100 for estimating cardiovascular information may extract, as pulse wave feature points, a valley point and a peak point of a first pulse wave DC component signal in the contact pressure transition period, a valley point and a peak point of a second pulse wave DC component signal in the contact pressure transition period, a valley point and a peak point of a differentiated first pulse wave DC component signal in the contact pressure transition period, a valley point and a peak point of a differentiated second pulse wave DC component signal in the contact pressure transition period, a valley point and a peak point of a first pulse wave AC component signal in the contact pressure transition period, a valley point and a peak point of a second pulse wave AC component signal in the contact pressure transition period, a valley point and a peak point of a DC component differential signal in the contact pressure transition period, a valley point and a peak point of a differentiated DC component differential signal in the contact pressure transition period, and the like.

The apparatus 100 for estimating cardiovascular information may extract cardiovascular characteristic values based on the extracted at least one pulse wave feature point in operation 1530. In one exemplary embodiment, the apparatus 100 for estimating cardiovascular information may extract cardiovascular characteristic values by using a pulse wave characteristic value, a contact pressure value, and the like which correspond to the extracted at least one pulse wave feature point. For example, the apparatus 100 for estimating cardiovascular information may extract cardiovascular characteristic values by linearly or non-linearly combining at least one or two or more of T1, T2, T3, T4, T5, T6, T7, T8, T9, T10, T11, T12, T13, T14, T15, T16, T17, T18, T19, T20, T21, T22, T23, T24, A1, A2, A3, A4, A5, A6, A7, A8, A9, A10, A11, A12, A13, A14, A15, A16, A17, A18, A19, A20, A21, A22, P1, P2, P3, P4, P5, P6, P7, P8, P9, P10, P11, P12, P13, P14, P15, P16, P17, P18, P19, P20, P21, P22, P23, P24, Pgmax, and Pgmin. Here, T1 denotes time of a valley point of a first pulse wave DC component signal in a contact pressure increasing period; T2 denotes time of a peak point of a first pulse wave DC component signal in a contact pressure increasing period; T3 denotes time of a valley point of a second pulse wave DC component signal in a contact pressure increasing period; T4 denotes time of a peak point of a second pulse wave DC component signal in a contact pressure increasing period; T5 denotes time of a valley point of a first pulse wave DC component signal in a contact pressure decreasing period; T6 denotes time of a peak point of a first pulse wave DC component signal in a contact pressure decreasing period; T7 denotes time of a valley point of a second pulse wave DC component signal in a contact pressure decreasing period; T8 denotes time of a peak point of a second pulse wave DC component signal in a contact pressure decreasing period; T9 denotes time of a valley point of a differentiated first pulse wave DC component signal in a contact pressure increasing period; T10 denotes time of a valley point of a differentiated second pulse wave DC component signal in a contact pressure increasing period; T11 denotes time of a peak point of a differentiated first pulse wave DC component signal in a contact pressure decreasing period; T12 denotes time of a peak point of a differentiated second pulse wave DC component signal in a contact pressure decreasing period; T13 denotes time of a peak point of a first pulse wave AC component signal in a contact pressure increasing period; T14 denotes time of a peak point of a second pulse wave AC component signal in a contact pressure increasing period; T15 denotes time of a valley point of a first pulse wave AC component signal in a contact pressure decreasing period; T16 denotes time of a valley point of a second pulse wave AC component signal in a contact pressure decreasing period; T17 denotes time of a peak point of a DC component differential signal in a contact pressure increasing period; T18 denotes time of a valley point of a DC component differential signal in a contact pressure increasing period; T19 denotes time of a peak point of a differentiated DC component differential signal in a contact pressure increasing period; T20 denotes time of a valley point of a DC component differential signal in a contact pressure decreasing period; T21 denotes time of a peak point of a DC component differential signal in a contact pressure decreasing period; T22 denotes time of a valley point of a differentiated DC component differential signal in a contact pressure decreasing period; T23 denotes time when contract pressure starts to increase; T24 denotes time when contract pressure starts to decrease; A1 denotes an amplitude of the first pulse wave DC component signal at T1; A2 denotes an amplitude of the first pulse wave DC component signal at T2; A3 denotes an amplitude of the second pulse wave DC component signal at T3; A4 denotes an amplitude of the second pulse wave DC component signal at T4; A5 denotes an amplitude of the first pulse wave DC component signal at T5; A6 denotes an amplitude of the first pulse wave DC component signal at T6; A7 denotes an amplitude of the second pulse wave DC component signal at T7; A8 denotes an amplitude of the second pulse wave DC component signal at T8; A9 denotes an amplitude of the differentiated first pulse wave DC component signal at T9; A10 denotes an amplitude of the differentiated second pulse wave DC component signal T10; A11 denotes an amplitude of the differentiated first pulse wave DC component signal T11; A12 denotes an amplitude of the differentiated second pulse wave DC component signal T12; A13 denotes an amplitude of the first pulse wave AC component signal T13; A14 denotes an amplitude of the second pulse wave AC component signal at T14; A15 denotes an amplitude of the first pulse wave AC component signal at T15; A16 denotes an amplitude of the second pulse wave AC component signal at T16; A17 denotes an amplitude of the DC component differential signal at T17; A18 denotes an amplitude of the DC component differential signal at T18; A19 denotes an amplitude of the differentiated DC component differential signal at T19; A20 denotes an amplitude of the DC component differential signal at T20; A21 denotes an amplitude of the DC component differential signal at T21; A22 denotes an amplitude of the differentiated DC component differential signal at T22; P1 denotes a contact pressure magnitude at T1; P2 denotes a contact pressure magnitude at T2; P3 denotes a contact pressure magnitude at T3; P4 denotes a contact pressure magnitude at T4; P5 denotes a contact pressure magnitude at T5; P6 denotes a contact pressure magnitude at T6; P7 denotes a contact pressure magnitude at T7; P8 denotes a contact pressure magnitude at T8; P9 denotes a contact pressure magnitude at T9; P10 denotes a contact pressure magnitude at T10; P11 denotes a contact pressure magnitude at T11; P12 denotes a contact pressure magnitude at T12; P13 denotes a contact pressure magnitude at T13; P14 denotes a contact pressure magnitude at T14; P15 denotes a contact pressure magnitude at T15; P16 denotes a contact pressure magnitude at T16; P17 denotes a contact pressure magnitude at T17; P18 denotes a contact pressure magnitude at T18; P19 denotes a contact pressure magnitude at T19; P20 denotes a contact pressure magnitude at T20; P21 denotes a contact pressure magnitude at T21; P22 denotes a contact pressure magnitude at T22; P23 denotes a contact pressure magnitude at T23; P24 denotes a contact pressure magnitude at T24; Pgmax denotes a maximum value of a contact pressure gradient in the contact pressure increasing period; and Pgmin denotes a minimum value of a contact pressure gradient in the contact pressure decreasing period.

Figure 16:
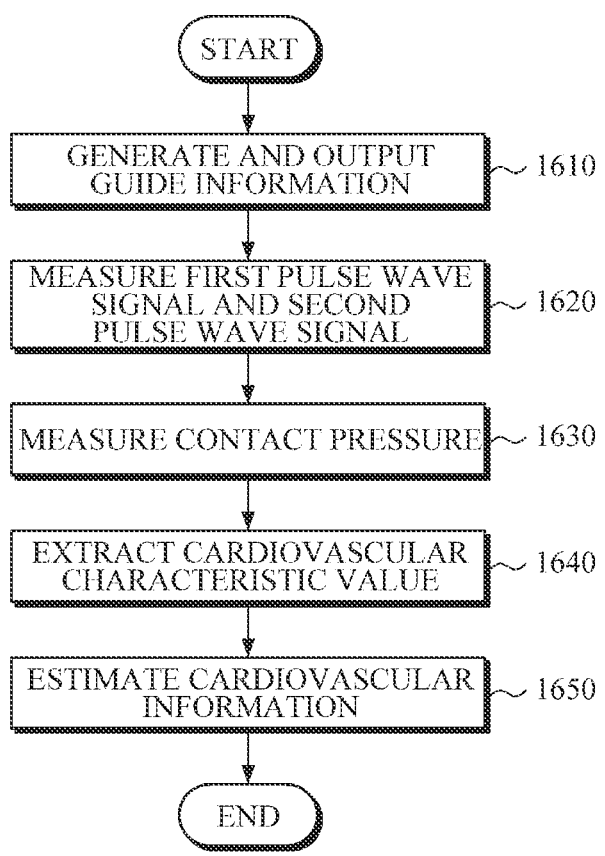
FIG. 16 is a flowchart illustrating a method of estimating cardiovascular information according to another exemplary embodiment.

FIG. 16 is a flowchart illustrating a method of estimating cardiovascular information according to another exemplary embodiment. The method of estimating cardiovascular information of FIG. 16 may be performed by the apparatus 100 for estimating cardiovascular information of FIG. 1.

Referring to FIGS. 1 and 16, the apparatus 100 for estimating cardiovascular information may generate and output guide information for guiding a user to increase or decrease contact pressure in operation 1610. For example, the apparatus 100 for estimating cardiovascular information may generate guide information illustrated in FIGS. 11 and 12.

The apparatus 100 for estimating cardiovascular information may measure a first pulse wave signal and a second pulse wave signal from an object by using light of different wavelengths in operation 1620, and may measure contact pressure between the object and the pulse wave measurer in operation 1630.

The apparatus 100 for estimating cardiovascular information may extract cardiovascular characteristic values based on the first pulse wave signal, the second pulse wave signal, and the contact pressure in operation 1640, and may estimate cardiovascular information based on the extracted cardiovascular characteristic values in operation 1650.

Figure 17:
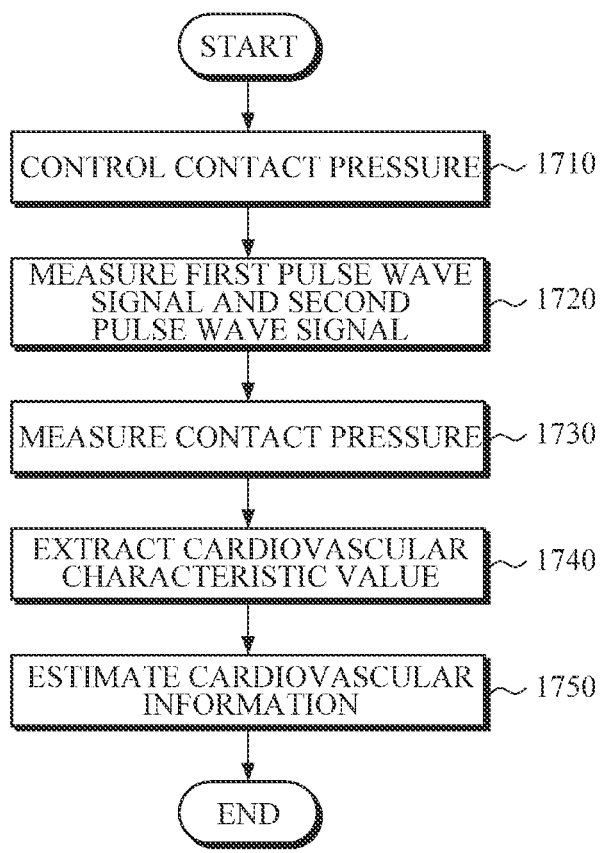
FIG. 17 is a flowchart illustrating a method of estimating cardiovascular information according to another exemplary embodiment.

FIG. 17 is a flowchart illustrating a method of estimating cardiovascular information according to another exemplary embodiment. The method of estimating cardiovascular information of FIG. 17 may be performed by the apparatus 1300 for estimating cardiovascular information of FIG. 13.

Referring to FIGS. 13 and 17, the apparatus 1300 for estimating cardiovascular information may control contact pressure between an object and a pulse wave measurer by using an actuator in operation 1710. For example, the apparatus 1300 for estimating cardiovascular information may increase the contact pressure between the object and the pulse wave measurer to a predetermined level, and after maintaining the contact pressure at the level for a predetermined period of time, the apparatus 1300 for estimating cardiovascular information may decrease the contact pressure.

The apparatus 1300 for estimating cardiovascular information may measure a first pulse wave signal and a second pulse wave signal from an object by using light of different wavelengths in operation 1720, and may measure contact pressure between the object and the pulse wave measurer in operation 1730.

The apparatus 1300 for estimating cardiovascular information may extract cardiovascular characteristic values based on the first pulse wave signal, the second pulse wave signal, and the contact pressure in operation 1740, and may estimate cardiovascular information based on the extracted cardiovascular characteristic values in operation 1750.

Figure 18:
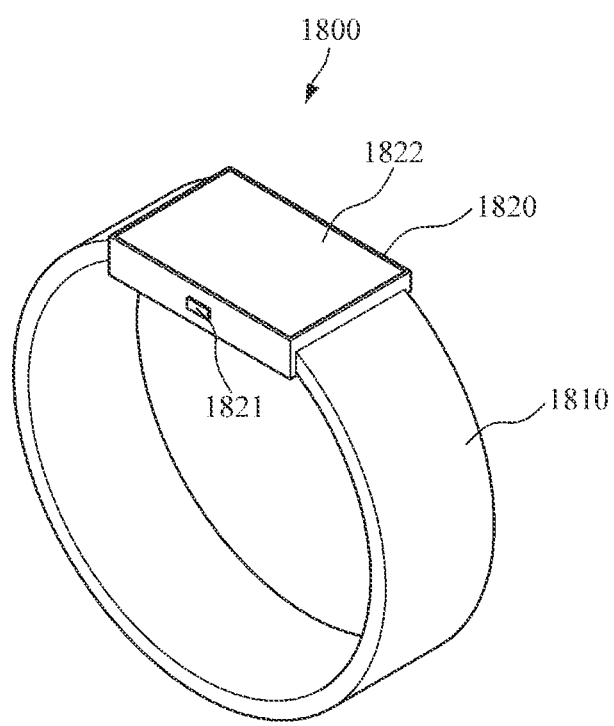
FIG. 18 is a perspective diagram of a wrist-type wearable device according to an exemplary embodiment.

FIG. 18 is a perspective diagram of a wrist-type wearable device according to another exemplary embodiment.

Referring to FIG. 18, the wrist-type wearable device 1800 includes a strap 1810 and a main body 1820.

The strap 1810 may be formed as a flexible band. However, this is merely exemplary, and the strap 1810 is not limited thereto. That is, the strap 1810 may be provided with various strap members which may be bent to be wrapped around a user's wrist.

The main body 1820 may include the above-described apparatuses 100 and 1300 for estimating cardiovascular information. Further, the main body 1820 may include a battery which supplies power to the wrist-type wearable device 1800 and the apparatuses 100 and 1300 for estimating cardiovascular information.

The wrist-type wearable device 1800 may further include an input interface 1821 and a display 1822 which are mounted in the main body 1820. The input interface 1821 may receive an input of various operation signals from a user. The display 1822 may display data processed by the wrist-type wearable device 1800 and the apparatuses 100 and 1300 for estimating cardiovascular information, processing result data, and the like.

Further, the main body 1820 may further include an actuator for controlling contact pressure between the pulse wave measurer and the object. The actuator may control the contact pressure between the pulse wave measurer and the object by adjusting the length of the strap 1810.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device, comprising:
a main body; and
a strap connected to the main body and formed to be flexible and to be wrapped around an object,
wherein the main body comprises:
a photoplethysmography (PPG) sensor configured to measure, from the object, a first pulse wave signal by using a first light of a first wavelength, and a second pulse wave signal by using a second light of a second wavelength, the first wavelength being different from the second wavelength;
a force sensor configured to measure a contact pressure between the object and the PPG sensor; and
a processor configured to:
obtain a cardiovascular characteristic value by calculating a change rate of the contact pressure with respect to time between a first point in time corresponding to a valley point of a direct current (DC) component signal of the first pulse wave signal and a second point in time corresponding to a valley point of a DC component signal of the second wave signal, during a contact pressure transition period in which the contact pressure continuously increases or continuously decreases; and
estimate blood pressure based on the cardiovascular characteristic value.

2. The wearable device of claim 1, wherein the main body further comprises an actuator configured to control the contact pressure between the object and the PPG sensor by adjusting a length of the strap.

3. A method of estimating cardiovascular information by using a photoplethysmography (PPG) sensor, the method comprising:
measuring a first pulse wave signal from an object by using a first light of a first wavelength;
measuring a second pulse wave signal from the object by using a second light of a second wavelength;
measuring a contact pressure between the object and the PPG sensor;
obtaining a cardiovascular characteristic value by calculating a change rate of the contact pressure with respect to time between a first point in time corresponding to a valley point of a direct current (DC) component signal of the first pulse wave signal and a second point in time corresponding to a valley point of a DC component signal of the second wave signal, during a contact pressure transition period in which the contact pressure continuously increases or continuously decreases; and
estimating blood pressure based on the cardiovascular characteristic value.

4. The method of claim 3, wherein the measuring the first pulse wave signal and the measuring the second pulse wave signal comprises:
emitting the first light and the second light onto the object; and
measuring the first pulse wave signal and the second pulse wave signal by receiving the first light and the second light which are reflected or scattered from the object, respectively.

5. The method of claim 3, wherein the contact pressure transition period comprises a contact pressure increasing period and a contact pressure decreasing period.

6. The method of claim 3, wherein the object is a user of the PPG sensor, and
wherein the method further comprises generating and outputting guide information about an action of the user for estimating the cardiovascular information.

7. The method of claim 3, further comprising controlling the contact pressure between the object and the PPG sensor.

8. A method of estimating cardiovascular information by using a photoplethysmography (PPG) sensor, the method comprising:
measuring a first pulse wave signal from an object by using a first light of a first wavelength;
measuring a second pulse wave signal from the object by using a second light of a second wavelength;
measuring a contact pressure between the object and the PPG sensor;
obtaining a cardiovascular characteristic value by calculating a change rate of the contact pressure with respect to time from a first point in time corresponding to a peak point of a direct current (DC) component signal of the first pulse wave signal, to a second point in time corresponding to a peak point of a DC component signal of the second pulse wave signal, during a contact pressure increasing period in which the contact pressure continuously increases; and
estimating blood pressure based on the cardiovascular characteristic value.

* * * * *